(12) United States Patent
Nishiyama et al.

(10) Patent No.: US 7,094,594 B2
(45) Date of Patent: Aug. 22, 2006

(54) PROCESS FOR PREPARING OPTICALLY ACTIVE 2-[6-(HYDROXY-METHYL)-1,3-DIOXAN-4-YL] ACETIC ACID DERIVATIVES

(75) Inventors: Akira Nishiyama, Kakogawa (JP); Miho Horikawa, Kobe (JP); Yoshihiko Yasohara, Himeji (JP); Noboru Ueyama, Kobe (JP); Kenji Inoue, Kakogawa (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/048,553

(22) PCT Filed: Jun. 5, 2001

(86) PCT No.: PCT/JP01/04729

§ 371 (c)(1),
(2), (4) Date: Oct. 18, 2004

(87) PCT Pub. No.: WO01/94337

PCT Pub. Date: Dec. 13, 2001

(65) Prior Publication Data

US 2005/0080277 A1    Apr. 14, 2005

(30) Foreign Application Priority Data

Jun. 5, 2000    (JP) ............................. 2000-168285

(51) Int. Cl.
*C12P 41/00*    (2006.01)
(52) U.S. Cl. .................................................... 435/280
(58) Field of Classification Search ................ 435/280
See application file for complete search history.

(56) References Cited

FOREIGN PATENT DOCUMENTS

| EP | 0 374 922 A2 | 6/1990 |
| EP | 0 577 040 A2 | 1/1994 |
| EP | 1 024 139 A1 | 8/2000 |
| JP | 4-173767 | 6/1992 |
| JP | 5-308977 | 11/1993 |
| WO | 00/08011 | * 2/2000 |
| WO | 01/85975 | * 11/2001 |

OTHER PUBLICATIONS

ATCC Catalog of Yeasts, p16 (1995).*
Morris et al., Separation Methods in Biochemistry, Pitman Publishing, Second Edition, p. 7 (1976).*
Machine Translation into English of JP 05-308977.*

* cited by examiner

*Primary Examiner*—Sandra E. Saucier
(74) *Attorney, Agent, or Firm*—Connolly, Bove, Lodge & Hutz, LLP

(57) ABSTRACT

The present invention is to provide a production technology by which an optically active 2-[6-(hydroxymethyl)-1, 3-dioxan-4-yl]acetic acid derivative, which are of value as pharmaceutical intermediates, can be produced from inexpensive and readily available starting materials without using any extraordinary equipment such as an ultra-low-temperature reactor.

The present invention is a production process of an optically active 2-[6-(hydroxymethyl)-1,3-dioxan-4-yl]acetic acid derivative
which comprises reacting an enolate, prepared by permitting a base or a 0-valent metal to act on an acetic acid ester derivative with (S)-β-hydroxy-γ-butyrolactone at a temperature not lower than −30° C. to give a dihydroxyoxohexanoic acid derivative,
treating the same with an acylating agent in the presence of a base to produce a dihydroxyoxohexanoic acid monoacyl derivative,
reducing this compound with a microorganism to produce a trihydroxyhexanoic acid monoacyl derivative,
treating this compound with an acetal-forming reagent in the presence of an acid catalyst to produce an acyloxymethyldioxanylacetic acid derivative, and
finally, subjecting this compound to solvolysis in the presence of a base.

44 Claims, No Drawings

PROCESS FOR PREPARING OPTICALLY ACTIVE 2-[6-(HYDROXY-METHYL)-1,3-DIOXAN-4-YL] ACETIC ACID DERIVATIVES

TECHNICAL FIELD

The present invention relates to a production process of pharmaceutical intermediates, particularly optically active 2-[6-(hydroxymethyl)-1,3-dioxan-4-yl]acetic acid derivatives of value as intermediates of HMG-CoA reductase inhibitors.

BACKGROUND ART

The hitherto-known technology for producing 2-[6-(hydroxymethyl)-1,3-dioxan-4-yl]acetic acid derivatives includes the following processes.

(1) A process starting with 3-hydroxy-γ-butyrolactone to synthesize a 3,5,6-trihydroxyhexanoic ester derivative via a 3,5-dihydroxyhexanoic ester derivative (JP-A-04-173767).

(2) A process starting with 3,4-dihydroxybutyronitrile acetonide to synthesize a 3,5,6-trihydroxyhexanoic ester derivative via a 3,5-dihydroxyhexanoic ester derivative (JP-A-02-262537).

(3) A process starting with a 4-chloroacetoacetic acid ester to synthesize a 3,5,6-trihydroxyhexanoic ester derivative through benzyloxylation, reduction, chain extension and like steps. (JP-A-06-65226).

(4) A process starting with a 4-chloro-3-hydroxybutyric ester to synthesize a 3,5,6-trihydroxyhexanoic ester derivative through chain extension, reduction and like steps. (U.S. Pat. No. 5,278,313).

(5) A process starting with malic acid to synthesize a 3,5,6-trihydroxyhexanoic ester derivative via a 2,4-dihydroxyadipic acid derivative (JP-A-04-69355).

However, these processes involve ultra-low temperature reactions around −80° C. in some stage or other of the respective production processes (1, 2, 4 and 5) or a high-pressure hydrogenation reaction requiring a pressure of as high as 100 kg/cm$^2$ (3), thus invariably requiring extraordinary reaction equipment. Moreover, expensive starting materials are used in some or other stages, so that none of the processes are efficient enough for industrial-scale production.

SUMMARY OF THE INVENTION

In the above state of the art, the object of the present invention is to provide a production technology by which an optically active 2-[6-(hydroxymethyl)-1,3-dioxan-4-yl]acetic acid derivative represented by the following formula (I), which are of value as pharmaceutical intermediates, can be produced with ease and high efficiency from inexpensive starting materials without using any extraordinary equipment such as an ultra-low-temperature reactor;

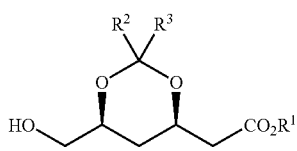
(I)

in the formula, $R^1$ represents a hydrogen, an alkyl group of 1 to 12 carbon atoms, an aryl group of 6 to 12 carbon atoms, or an aralkyl group of 7 to 12 carbon atoms; $R^2$ and $R^3$ each independently represents a hydrogen, an alkyl group of 1 to 12 carbon atoms, an aryl group of 6 to 12 carbon atoms, or an aralkyl group of 7 to 12 carbon atoms; and $R^2$ and $R^3$ may jointly form a ring.

Under the circumstances, the inventors of the present invention carried out intensive investigations and, as a consequence, developed an expedient technology for producing optically active 2-[6-(hydroxymethyl)-1,3-dioxan-4-yl]acetic acid derivatives of the following formula (I) from inexpensive, readily available starting materials without using any extraordinary equipment such as an ultra-low-temperature reactor;

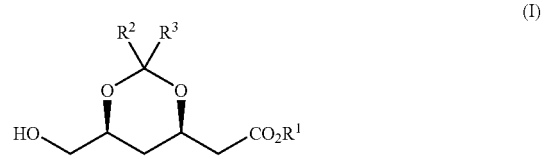
(I)

in the formula, $R^1$ represents a hydrogen, an alkyl group of 1 to 12 carbon atoms, an aryl group of 6 to 12 carbon atoms, or an aralkyl group of 7 to 12 carbon atoms; $R^2$ and $R^3$ each independently represents a hydrogen, an alkyl group of 1 to 12 carbon atoms, an aryl group of 6 to 12 carbon atoms, or an aralkyl group of 7 to 12 carbon atoms; and $R^2$ and $R^3$ may jointly form a ring.

The present invention, therefore, is directed to a production process of an optically active 2-[6-(hydroxymethyl)-1,3-dioxan-4-yl]acetic acid derivative represented by the general formula (I);

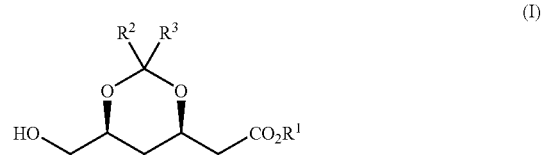
(I)

in the formula, $R^1$, $R^2$ and $R^3$ are as defined above,
which comprises
(1) reacting an enolate prepared by permitting a base or a 0-valent metal to act on an acetic acid ester derivative represented by the following formula (II);

$$X^1CH_2CO_2R^1 \quad (II)$$

in the formula, $R^1$ is as defined above; and $X^1$ represents a hydrogen or a halogen atom,
with (S)-β-hydroxy-γ-butyrolactone represented by the following formula (III);

(III)

at a temperature not lower than −30° C. to produce a compound represented by the following formula (IV);

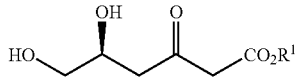

in the formula, $R^1$ is as defined above, (2) treating this compound with an acylating agent in the presence of a base to produce a compound represented by the following formula (V);

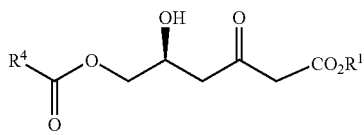

in the formula, $R^1$ is as defined above; and $R^4$ represents a hydrogen, an alkyl group of 1 to 12 carbon atoms, an aryl group of 6 to 12 carbon atoms, or an aralkyl group of 7 to 12 carbon atoms, (3) reducing this compound with a microorganism to produce a compound represented by the following formula (VI);

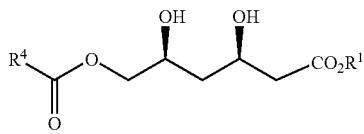

in the formula, $R^1$ and $R^4$ are as defined above, (4) treating this compound with an acetal-forming reagent in the presence of an acid catalyst to produce a compound represented by the following formula (VII);

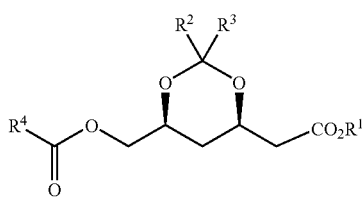

in the formula, $R^1$, $R^2$, $R^3$, and $R^4$ are as defined above, and (5) subjecting this compound to solvolysis in the presence of a base.

The present invention is also directed to an isolation/purification process which comprises treating a compound contaminated with an impurity and represented by the following formula (V);

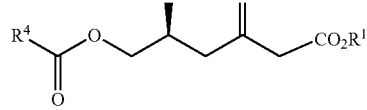

in the formula, $R^1$ represents a hydrogen, an alkyl group of 1 to 12 carbon atoms, an aryl group of 6 to 12 carbon atoms, or an aralkyl group of 7 to 12 carbon atoms; and $R^4$ represents a hydrogen, an alkyl group of 1 and 12 carbon atoms, an aryl group of 6 to 12 carbon atoms, or an aralkyl group of 7 and 12 carbon atoms, with an aliphatic hydrocarbon solvent to remove the impurity contaminating the compound represented by the above formula (V) and obtaining the compound represented by the above formula (V) in a crystal form.

Furthermore, the present invention is directed to a production process of a compound represented by the following formula (VI);

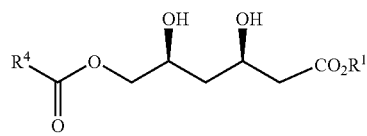

in the formula, $R^1$ and $R^4$ are as defined above, which comprises reducing a compound represented by the following formula (V);

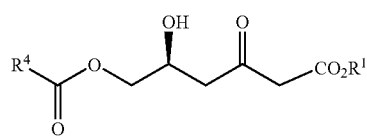

in the formula, $R^1$ and $R^4$ are as defined above, with a microorganism.

In another aspect, the present invention is directed to a production process of a compound represented by the following formula (VII);

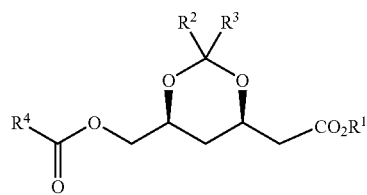

in the formula, $R^1$, $R^2$, $R^3$ and $R^4$ are as defined above, which comprises treating a compound represented by the following formula (VI);

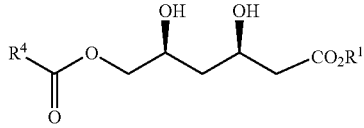
(VI)

in the formula, $R^1$ and $R^4$ are as defined above,
with an acetal-forming reagent using an amine salt composed of an acid and an amine as a catalyst.

In still another aspect, the present invention is directed to an isolation/purification process which comprises treating a compound represented by the following formula (VI);

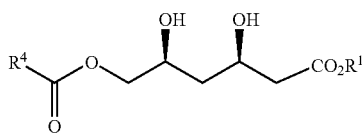
(VI)

in the formula, $R^1$ and $R^4$ are as defined above,
with an acetal-forming reagent in the presence of an acid catalyst to thereby convert the same to a compound represented by the following formula (VII);

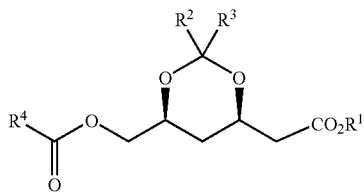
(VII)

in the formula, $R^1$, $R^2$, $R^3$ and $R^4$ are as defined above, treating the compound contaminated with an impurity and represented by the above formula (VII) with an aliphatic hydrocarbon solvent to remove the impurity contaminating the compound represented by the above formula (VII) and obtaining the compound represented by the above formula (VII) in a crystal form.

DISCLOSURE OF INVENTION

The present invention is now described in detail.

As illustrated in the following reaction scheme, the present invention comprises five non-ultra-low temperature reaction steps (1) through (5).

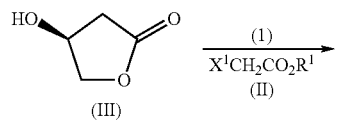

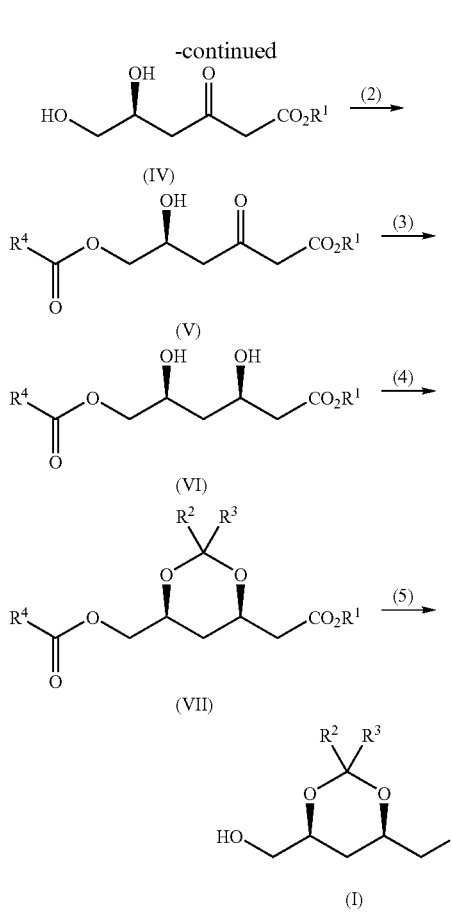

The present invention is now described, step by step, in detail.

Step (1)

In this step, an enolate prepared by permitting a base or a 0-valent metal to act on an acetic acid ester derivative represented by the following formula (II);

$$X^1CH_2CO_2R^1 \qquad (II)$$

is reacted with (S)-β-hydroxy-γ-butyrolactone represented by the following compound (III);

(III)

at a temperature not lower than −30° C. to produce a (5S)-configured dihydroxyoxohexanoic acid derivative represented by the following formula (IV);

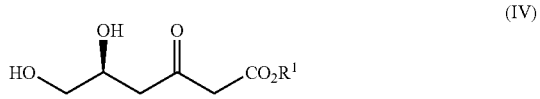
(IV)

Generally when a reaction involving the enolate of an acetic acid ester or the like is carried out in a non-ultra-low temperature reaction over, for example, not lower than −30° C., the self-condensation of the enolate proceeds preferentially to markedly sacrifice the conversion rate of the objective reaction. However, it was found that according to the following technique developed by the present inventors, the self-condensation of the acetic acid enolate can be minimized and the objective reaction can be carried through with good product yield.

(S)-β-hydroxy-γ-butyrolactone, which is used in the step (1), can be produced in a large scale by the known technology (e.g. SYNTHETIC COMMUNICATION, 1986, 16, 183.).

Referring to the acetic acid ester derivative for use in the step (1), $R^1$ represents a hydrogen, an alkyl group of 1 to 12 carbon atoms, an aryl group of 6 to 12 carbon atoms, or an aralkyl group of 7 to 12 carbon atoms, and more specifically, including a hydrogen, methyl, ethyl, i-propyl, tert-butyl, n-octyl, phenyl, naphthyl, p-methoxyphenyl, p-nitrobenzyl, and like groups. The preferred is a tert-butyl group. $X^1$ represents a hydrogen or a halogen atom, and more specifically including a hydrogen, a chlorine, a bromine, and an iodine, preferably a hydrogen and a bromine.

The level of use of the acetic acid ester derivative relative to (S)-β-hydroxy-γ-butyrolactone is 1 molar equivalent to 10 molar equivalents, preferably 1 molar equivalent to 5 molar equivalents.

In the step (1), a base or a 0-valent metal is permitted to act on the acetic acid ester derivative to prepare an enolate. Generally speaking, in preparing the enolate, a base is used when $X^1$ of the acetic acid ester is a hydrogen; a 0-valent metal is used in preparing the enolate when $X^1$ is a halogen atom.

The base which is used in preparing the enolate includes, for example, lithium amides such as lithium amide, lithium diisopropylamide, lithium dicyclohexylamide, lithium hexamethyldisilazide, etc.; magnesium amides such as chloromagnesium diisopropylamide, bromomagnesium diisopropylamide, iodomagnesium diisopropylamide, chloromagnesium dicyclohexylamide, etc.; sodium amides such as sodium amide, sodium diisopropylamide, etc.; potassium amides such as potassium amide, potassium diisopropylamide, etc.; alkyllithiums such as methyllithium, n-butyllithium, phenyllithium, tert-butyllithium, etc.; Grignard reagents such as methylmagnesium bromide, phenylmagnesium chloride, iso-propylmagnesium chloride, tert-butylmagnesium chloride, etc.; metal alkoxides such as sodium methoxide, magnesium ethoxide, potassium tert-butoxide, etc.; and metal hydrides such as lithium hydride, sodium hydride, potassium hydride, calcium hydride, and so forth. The preferred are metal hydrides, magnesium amides, lithium amides and Grignard reagents. These bases can be used each independently or in combination. For example, a lithium amide or a metal hydride is effective when used in combination with a magnesium-containing base such as a Grignard reagent or a magnesium amide. Moreover, said magnesium-containing base may be prepared in situ from a base and a magnesium compound such as magnesium chloride, magnesium bromide, or the like.

The magnesium amide is represented by the general formula (VIII);

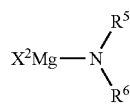

in the above formula, $R^5$ and $R^6$ each independently represents an alkyl group of 1 to 12 carbon atoms, an aryl group of 6 to 12 carbon atoms, an aralkyl group of 7 to 12 carbon atoms, or a silyl group. Specifically, there can be mentioned methyl, ethyl, i-propyl, tert-butyl, cyclohexyl, n-octyl, phenyl, naphthyl, p-methoxyphenyl, p-nitrobenzyl, trimethylsilyl, triethylsilyl, phenyldimethylsilyl, and like groups. The preferred is an isopropyl group. $X^2$ represents a halogen atom and is preferably a chlorine, a bromine, or an iodine. The more preferred is a chlorine.

It is to be understood that the magnesium amide can be prepared from an inexpensive, readily available secondary amine and a Grignard reagent by the known technology (for example, JP-A-08-523420). As an alternative, it can be prepared from lithium amide and a magnesium halide by the known technology (e.g. J. Org. Chem. 1991, 56, 5978–5980).

The Grignard reagent is represented by the following formula (IX);

in the above formula, $R^7$ represents an alkyl group of 1 to 12 carbon atoms, an aryl group of 6 to 12 carbon atoms, or an aralkyl group of 7 to 12 carbon atoms. Specifically, there can be mentioned methyl, ethyl, n-propyl, i-propyl, n-butyl, tert-butyl, n-octyl, phenyl, naphthyl, p-methoxyphenyl, p-nitrobenzyl and like groups. The preferred groups include methyl, ethyl, i-propyl, n-butyl, tert-butyl and so forth. $X^3$ represents a halogen atom and preferably is a chlorine, a bromine, or an iodine. The more preferred is a chlorine.

The lithium amide is represented by the general formula (X);

in the above formula, $R^8$ and $R^9$ each independently represents an alkyl group of 1 to 12 carbon atoms, an aryl group of 6 to 12 carbon atoms, an aralkyl group of 7 to 12 carbon atoms, or a silyl group. Specifically, there can be mentioned methyl, ethyl, i-propyl, tert-butyl, cyclohexyl, n-octyl, phenyl, naphthyl, p-methoxyphenyl, p-nitrobenzyl, trimethylsilyl, triethylsilyl, phenyldimethylsilyl and like groups. The preferred is an isopropyl group.

The level of use of the base in the step (1), relative to (S)-β-hydroxy-γ-butyrolactone, is 1 molar equivalent to 20 molar equivalents, preferably 2 molar equivalent to 8 molar equivalents.

The 0-valent metal usable in preparing the enolate of the step (1) includes zinc, magnesium, tin, etc., although zinc and magnesium are preferred. The level of use of the 0-valent metal relative to (S)-β-hydroxy-γ-butyrolactone is 1 molar equivalent to 20 molar equivalents, preferably 2 molar equivalent to 8 molar equivalents.

The solvent usable in the step (1) includes, for example, aprotic organic solvents. As such organic solvents, there can be mentioned, for example, hydrocarbon solvents such as benzene, toluene, n-hexane, cyclohexane, etc.; ether solvents such as diethyl ether, tetrahydrofuran, 1,4-dioxane, methyl t-butyl ether, dimethoxyethane, ethylene glycol dimethyl ether, etc.; halogenated hydrocarbon solvents such as methylene chloride, chloroform, 1,1,1-trichloroethane, etc.;

and aprotic polar solvents such as dimethylformamide, N-methylpyrrolidone, hexamethylphosphoric triamide, and so forth. The above solvents may be used each independently or in a combination of two or more species. The preferred, among the above-mentioned solvents, are hydrocarbon solvents such benzene, toluene, n-hexane, cyclohexane, etc.; and ether solvents such as diethyl ether, tetrahydrofuran, 1,4-dioxane, methyl t-butyl ether, dimethoxyethane, diethylene glycol dimethyl ether, and so forth. The more preferred are polyether solvents such as dimethoxyethane, diethylene glycol dimethyl ether, and so forth. These polyether solvents may be used each as a sole solvent or added, as an addendum, to another reaction solvent, at the level of about 1 molar equivalent to about 10 molar equivalents relative to (S)-β-hydroxy-γ-butyrolactone.

The reaction temperature to be used in the step (1) is preferably −30° C. to 100° C., more preferably −10° C. to 60° C.

In the step (1), the order of mixing the reactants may be random but it is preferred to treat (S)-β-hydroxy-γ-butyrolactone with a base, more preferably with a base and a magnesium compound in advance. The preferred base includes metal hydrides and lithium amides. The preferred magnesium compound includes magnesium chloride, magnesium bromide, magnesium sulfate, and so forth. A magnesium-containing base may be used so that it will double as the base and the magnesium compound. The magnesium-containing base includes, for example, Grignard reagents such as methylmagnesium bromide, iso-propylmagnesium chloride, phenylmagnesium chloride, tert-butylmagnesium chloride, etc. and magnesium amides such as chloromagnesium diisopropylamide, bromomagnesium diisopropylamide, iodomagnesium diisopropylamide, chloromagnesium dicyclohexylamide and so forth. The preferred is tert-butylmagnesium chloride.

The level of use of the base in this pretreatment, relative to (S)-β-hydroxy-γ-butyrolactone, is 0.01 molar equivalent through 3 molar equivalents, preferably 0.5 molar equivalent to 1.5 molar equivalents.

The level of use of the magnesium compound in the pretreatment, relative to (S)-β-hydroxy-γ-butyrolactone, is 0.01 molar equivalent to 3 molar equivalents, preferably 0.5 molar equivalent to 1.5 molar equivalents.

The level of use of the magnesium-containing base in the pretreatment, relative to (S)-β-hydroxy-γ-butyrolactone, is 0.01 molar equivalent to 3 molar equivalents, preferably 0.5 molar equivalent to 1.5 molar equivalents.

The pretreatment of (S)-β-hydroxy-γ-butyrolactone with the base may be carried out on a mixed solution of (S)-β-hydroxy-γ-butyrolactone and an acetic acid ester derivative. After the pretreatment, the reaction may be conducted under dropwise addition of a base, such as a lithium amide, e.g. lithium amide, lithium diisopropylamide, lithium dicyclohexylamide, lithium hexamethyldisilazide or the like or a magnesium amide, e.g. diisopropylmagnesium chloride, diisopropylmagnesium bromide or the like, or a solution of the base.

The level of the base to be reacted after the pretreatment, relative to (S)-β-hydroxy-γ-butyrolactone, is 1 molar equivalent to 20 molar equivalents, preferably 2 molar equivalents to 8 molar equivalents.

Thus, the step (1) can be carried out with advantage by pretreating (S)-β-hydroxy-γ-butyrolactone with the base and the magnesium compound in advance followed by permitting the base to act in the presence of the acetic acid ester derivative. As an alternative, (S)-β-hydroxy-γ-butyrolactone may be treated with the base in advance and reacted with the enolate prepared by permitting a 0-valent metal to act on the acetic acid ester derivative.

The after-treatment following the step (1) may be an after-treatment which is generally carried out for recovery of the product from a reaction mixture. For example, the reaction mixture available on completion of the reaction is mixed with the common inorganic or organic solvent, e.g. hydrochloric acid, sulfuric acid, nitric acid, acetic acid or citric acid followed by extraction with the common extractant solvent, e.g. ethyl acetate, diethyl ether, methylene chloride, toluene, or hexane. From the extract thus obtained, the reaction solvent and the extractant solvent are removed by heating under reduced pressure or the like procedure to give the objective compound. The objective compound thus obtained may further be purified by the routine technique such as crystallization, fractional distillation or column chromatography but it can be transmitted directly to the next step without isolation.

Step (2)

In this step, the dihydroxyoxohexanoic acid derivative represented by the following formula (IV);

(IV)

as obtained in the step (1), is treated with an acylating agent in the presence of a base to produce a dihydroxyoxohexanoic acid monoacyl derivative represented by the following formula (V);

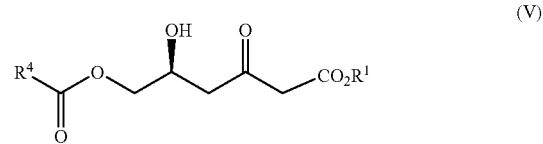

(V)

As the acylating agent usable in the step (2), any of a compound represented by the following formula (XI);

(XI)

and a compound represented by the following formula (XVI);

(XVI)

can be used. In the above formulas, $R^4$ represents a hydrogen, an alkyl group of 1 to 12 carbon atoms, an aryl group of 6 to 12 carbon atoms, or an aralkyl group of 7 to 12 carbon atoms. Specifically, there may be mentioned a hydrogen, methyl, ethyl, n-propyl, i-propyl, n-butyl, tert-butyl, n-octyl, phenyl, naphthyl, p-methoxyphenyl, p-nitrobenzyl, and like groups. The preferred are methyl, ethyl, i-propyl, tert-butyl, and phenyl groups, with a phenyl group being particularly preferred.

Q represents a leaving group. Specifically, there can be mentioned a halogen atom, e.g. chlorine, bromine, iodine, etc.; an alkoxycarbonyloxy group, e.g. methoxycarbonyloxy, ethoxycarbonyloxy, tert-butoxycarbonyloxy, etc.; a cyano group; an imidazolido group, and so forth. The preferred is a chlorine.

The level of use of the acylating agent relative to the dihydroxyoxohexanoic acid derivative is preferably 0.5 to 2 molar equivalents, more preferably 0.8 to 1.5 molar equivalents.

The base which can be used in the step (2) includes inorganic bases such as sodium carbonate, potassium carbonate, sodium hydrogen carbonate, potassium hydrogen carbonate, sodium hydroxide, potassium hydroxide, calcium hydroxide, lithium hydroxide, barium hydroxide, magnesium hydroxide, etc.; ammonia and amines such as triethylamine, pyridine, N-methylmorpholine, diisopropylethylamine, N,N-dimethylaminopyridine, etc., with triethylamine or pyridine being preferred. The level of use of the base relative to the dihydroxyoxohexanoic acid derivative is preferably 1 to 10 molar equivalents, more preferably 1 to 3 molar equivalents.

The reaction solvent which can be used in the step (2) includes hydrocarbon solvents such as benzene, toluene, cyclohexane, etc.; ether solvents such as diethyl ether, tetrahydrofuran, 1,4-dioxane, methyl tert-butyl ether, dimethoxyethane, etc.; ester solvents such as ethyl acetate, butyl acetate, etc.; ketone solvents such as acetone, methyl ethyl ketone, etc.; halogenated hydrocarbon solvents such as methylene chloride, chloroform, 1,1,1-trichloroethane, etc.; nitrogen-containing solvents such as dimethylformamide, acetamide, formamide, acetonitrile, etc.; and aprotic polar solvents such as dimethyl sulfoxide, N-methylpyrrolidone, hexamethylphosphoric triamide, and so forth. The above-mentioned organic solvents may be used each independently or in a combination of two or more species. The preferred are toluene, ethyl acetate, acetone, methylene chloride, methyl tert-butyl ether, tetrahydrofuran, dimethylformamide, acetonitrile, and so forth.

The reaction temperature in the step (2) is −30° C. to 80° C., preferably −10° C. to 40° C.

The after-treatment following the step (2) may be an after-treatment which is generally carried out for recovery of the product from the reaction mixture on completion of the reaction. For example, the reaction mixture available on completion of the reaction is added with water and extraction procedure is carried out with the common extractant solvent, such as ethyl acetate, diethyl ether, methylene chloride, toluene, hexane or the like. From the extract thus obtained, the reaction solvent and extractant solvent are removed by heating under reduced pressure or the like procedure to obtain the objective compound.

The objective compound thus obtained tends to contain various impurities originating from various decompositions and side reactions which take place in the course of production. Particularly, the dihydroxyoxohexanoic acid diacyl derivative of the following general formula (XII);

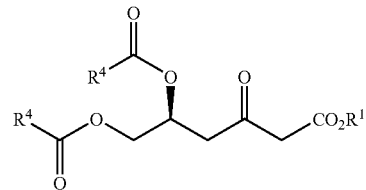

(XII)

($R^1$ and $R^4$ are as defined hereinbefore) tends to be by-produced as a major impurity and in order that the objective compound of high quality grade may be isolated, such impurities must be somehow removed. Generally, however, an impurity structurally resembling the objective compound (structural analog) is not easy to remove, and in order that such impurities may be removed to give the objective compound of high purity grade, a good protocol for purification and isolation is required. The inventors of the present invention found that said impurities can be efficiently removed by carrying out a crystallization procedure under the conditions described below.

The crystallization solvent for use in the present invention is preferably an aliphatic hydrocarbon solvent. Specifically, aliphatic hydrocarbons containing 5–20 carbon atoms, such as pentane, petroleum ether, neopentane, hexane, cyclohexane, methylcyclohexane, heptane, cycloheptane, octane, isooctane, nonane, decane, undecane, dodecane, etc. can be mentioned. Among these, pentane, hexane, methylcyclohexane, heptane, octane, and isooctane are preferred. These may be used each independently or in a combination of two or more species.

Particularly in terms of the ease of removal of the solvent from wet crystals by desiccation or the recovery and reuse of the solvent (distillative recovery), the use of a solvent having a comparatively low boiling point is preferred. As such solvents, solvents having a boiling point of not higher than about 100° C. at atmospheric or subatmospheric pressure can generally be mentioned. More particularly, aliphatic hydrocarbon solvents of 5–8 carbon atoms, such as pentane, hexane, methylcyclohexane, heptane, octane and isooctane, etc. can be mentioned, and when the cost of the solvent, ease of handling, and other factors are globally taken into consideration, hexane and methylcyclohexane are particularly preferred.

The use of the above aliphatic hydrocarbon solvent provides for the stabilization and assurance of a high yield of the objective compound as well as a high degree of purification, that is to say effective removal of various impurities, particularly said compound (XII). The level of use of said aliphatic hydrocarbon solvent is preferably such that, at completion of the procedure for crystallization of said compound (V), the fluidity of the obtained product can be retained, and may, for example, be about 5 to 20 parts by weight, or even more in some cases, relative to said compound (V).

For the crystallization of said compound (V) in the present invention, crystallization by cooling, crystallization by concentration, and other methods for crystallization can be used each independently or in combination. The crystallization by concentration, mentioned above, may be a crystallization procedure in which a solution composed of a solvent other than said aliphatic hydrocarbon solvent is converted to a solution composed of said aliphatic hydrocarbon solvent. Moreover, seed crystals may be added in this crystallization procedure.

In the present invention, for the purpose of improving at least one of a solubility, yield, treatment concentration, purification effect (efficiency of impurity removal), and physical properties of obtainable crystals of the above compound (V), an auxiliary solvent can be used in addition to said aliphatic hydrocarbon solvent in conducting the crystallization procedure. The above auxiliary solvent may be added to said aliphatic hydrocarbon solvent as necessary or the compound (V) may be dissolved in the auxiliary solvent in advance and the solution added to said aliphatic hydrocarbon solvent.

The auxiliary solvent mentioned above is not particularly restricted but includes, for example, acetone, methyl ethyl ketone, tetrahydrofuran, methyl tert-butyl ether, ethyl acetate, isopropyl acetate, tert-butyl acetate, ethanol, isopropanol, toluene, benzene, xylene, chlorobenzene, methylene chloride, chloroform, and 1,2-dichloroethane, etc. These may be used each independently or in a combination of two or more species. Among these, ethyl acetate, toluene, methyl tert-butyl ether, methylene chloride, etc. can contribute to increased solubility and improved treatment parameters such as treatment concentration and purification effect.

The auxiliary solvent mentioned above expresses its effect more prominently when used in a suitable amount combined with said aliphatic hydrocarbon solvent, which suitable amount being established according to the characteristics of the auxiliary solvent in relation to the desired effect and other factors. The optimal level of use of said auxiliary solvent can be found by simple experimentation. From the standpoint of yield and purification effect, the level of use of the above auxiliary solvent is preferably such that the weight ratio of said auxiliary solvent and said aliphatic hydrocarbon solvent (auxiliary solvent/aliphatic hydrocarbon solvent) is not greater than 1 at completion of the procedure for crystallization of said compound (V). The more preferred level is such that e ratio id 0.5 or less.

The purification/isolation process according to the present invention can be carried out in the neighborhood of room temperature. Where necessary, warming or cooling can be carried out, for example at a temperature not over about 60° C., usually at −30° C. to 50° C.

The above compound (V) thus obtained is separated by a solid-liquid separation technique, optionally further followed by cake washing and drying. The solid-liquid separation technique is not particularly restricted but includes, for example, filtration under pressure, suction filtration, centrifugation, and so forth. The above drying is preferably carried out under reduced pressure (drying in vacuo) at a temperature not exceeding about 60° C. in order to avoid pyrolysis or fusion, for instance.

Step (3)

In this step, the (5S)-configured dihydroxyoxohexanoic acid monoacyl derivative represented by the following formula (V);

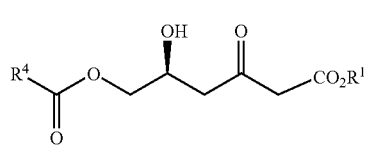

as obtained in said step (2) is reduced using a microorganism to give a (3R,5S)-configured trihydroxyhexanoic acid monoacyl derivative represented by the following formula (VI);

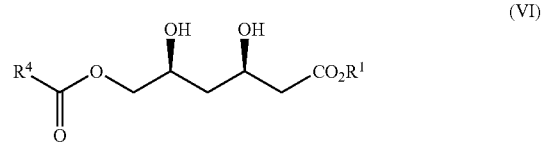

Generally for the highly stereoselective reduction of the carbonyl group of a dihydroxyoxohexanoic acid monoacyl derivative such as the above compound, the reduction process using a hydride series reducing agent, such as sodium borohydride, in the presence of an alkylborane at an ultralow temperature is employed (e.g. JP-A-02-262537).

For the purpose of reducing a dihydroxyoxohexanoic acid monoacyl derivative stereoselectively under non-ultra-low temperature conditions at low cost, the inventors of the present invention developed a reduction method using a microorganism.

The microorganism capable of reducing dihydroxyoxohexanoic acid monoacyl derivatives to the corresponding trihydroxyhexanoic acid monoacyl derivatives, which is to be used in the step (3), can be found by the methods described below. Taking a yeast as an example, there can be used, for example, the method which comprises charging a large test tube with 5 ml of Medium A (pH 7.0) of the composition: glucose 3%, yeast extract 0.3%, potassium dihydrogen phosphate 0.7%, diammonium hydrogen phosphate 1.3%, magnesium sulfate.$7H_2O$ 0.08%, zinc sulfate.$7H_2O$ 0.007%, iron sulfate.$7H_2O$ 0.009%, copper sulfate.$5H_2O$ 0.0005%, manganese sulfate.$4H_2O$ 0.001%, and sodium chloride 0.01%, sterilizing the medium, inoculating a yeast, carrying out a shake culture at 27° C. for 2 to 3 days, harvesting the grown cells by centrifugation, suspending the cells in 0.5 ml of phosphate buffer containing 0.01 to 1% of (5S)-6-benzoyloxy-5-hydroxy-3-oxohexanoic acid tert-butyl ester and 8% of glucose, and shaking the suspension in a large test tube at 27° C. for 1 to 3 days. For the identification of the objective reducing ability, the reaction mixture after shake culture is extracted with ethyl acetate and the organic phase is analyzed by high performance liquid chromatography [column: Dovelosil ODS-HG-3 (4.6 mm×150 mm) (product of Nomura Chemical), eluent: 0.1% trifluoroacetic acid/acetonitrile=6/4, flow rate: 0.8 ml/min, detection: 210 nm, column temperature: room temperature, elution time: (3S,5S)-6-benzoyloxy-3,5-dihydroxyhexanoic acid tert-butyl ester; 10.1 min, (3R,5S)-6-benzoyloxy-3,5-dihydroxyhexanoic acid tert-butyl ester; 11.0 min, and (5S)-6-benzoyloxy-5-hydroxy-3-oxohexanoic acid tert-butyl ester; 16.7 min; it is to be understood that these conditions are for illustrative purposes only]. When the candidate microorganism is a bacterial strain, Medium B (pH 7.0) of the composition: glycerol 1.5%, Proextract 1.0%, and yeast extract 0.5%, for instance, is employed, for instance. In the case of a fungal strain, Medium C (pH 6.0) of the composition: glucose 5% and corn steep liquor 5% is employed, for instance. In the case of an actinomycete, Medium D (pH 7.2) of the composition: Difco-tryptic soy broth 3% and soluble starch 1% is employed. Using these media, the respective strains of microorganisms are cultured, and the microorganisms having the objective ability are selected by the same procedure as described above.

The microorganism which can be used in the practice of the present invention includes microorganisms belonging to the genera: *Ashbya, Botryoascus, Brettanomyces, Candida, Citeromyces, Clavispora, Cryptococcus, Debaryomyces, Dekkera, Dipodascus, Galactomyces, Geotrichum, Hanseniaspora, Hansenula, Hormoascus, Hyphopichia, Issatchenkia, Kluyveromyces, Komagataella, Lipomyces, Metschnikowia, Nakazawaea, Ogataea, Pachysolen, Pichia, Rhodotorula, Rhodsporidium, Saccharomyces, Saccharomycodes, Saccharomycopsis, Saturnospora, Schizoblastosporion, Schizosaccharomyces, Schwanniomyces, Sporidiobolus, Sporobolomyces, Torulaspora, Torulopsis, Trichosporon, Trigonopsis, Willopsis, Yamadazyma, Zygosaccharomyces, Acidiphilium, Aerobacter, Alcaligenes, Arthrobacter, Aureobacterium, Bacillus, Brevibacterium, Buttiauxella, Cedecea, Cellulomonas, Citrobacter, Clostridium, Comamonas, Corynebacterium, Enterobacter, Erwinia, Escherichia, Flavobacterium, Klebsiella, Luteococcus, Microbacterium, Micrococcus, Ochrobactrum, Proteus, Providencia, Pseudomonas, Rhodococcus, Sarcina, Serratia, Sphingobacterium, Tsukamurella, Absidia, Acremonium, Aegerita, Agrocybe, Amylostereum, Aspergillus, Byssochlamys, Chaetomidium, Chaetosartorya, Cladosporium, Coprinus, Crinipellis, Endophragmia, Flavolus, Fomitopsis, Fusarium, Ganoderma, Glomerella, Laetiporus, Lentinus, Lenzites, Macrophoma, Monascus, Mortierella, Paecilomyces, Penicillium, Phialophora, Pholiota, Pleurotus, Scopulariopsis, Sehizophyllum, Sporotrichum, Zygorhynchus, Microtetraspora*, and *Streptomyces*. More particularly, the usable are, for example, *Ashbya gossypii* IFO 0560, *Botryoascus synnaedendrus* IFO 1604, *Brettanomyces custersianus* IFO 1585, *Candida arborea* IAM 4147, *Candida catenulata* IFO 0745, *Candida fennica* CBS 6028, *Candida galacta* IFO 10031, *Candida haemulonii* IFO 10001, *Candida magnoliae* IFO 0705, *Candida musae* IFO 1582, *Candida nitratophila* IFO 10004, *Candida parapsilosis* IFO 0585, *Candida pararugosa* IFO 0966, *Candida stellata* IFO 0701, *Citeromyces matritensis* IFO 0651, *Clavispora lusitaniae* IFO 1019, *Cryptococcus laurentii* IFO 0609, *Debaryomyces carsonii* IFO 0795, *Debaryomyces hansenii* var. *fabryi* IFO 0794, *Debaryomyces hansenii* var. *hansenii* IFO 0032, *Debaryomyces hansenii* var. *hansenii* IFO 0047, *Debaryomyces hansenii* var. *hansenii* IFO 0018, *Debaryomyces kloeckeri, Debaryomyces marama* IFO 0668, *Debaryomyces pseudopolymorphus* IFO 1026, *Debaryomyces robertsiae* IFO 1277, *Debaryomyces* sp. IFO 0025, *Dekkera anomala* IFO 0627, *Dipodascus armillariae* IFO 0102, *Dipodascus ovetensis* IFO 1201, *Dipodascus tetrasperma* CBS 765.70, *Galactomyces reessii* CBS 179.60, *Geotrichum candidum* CBS 187.67, *Geotrichum fermentans* IFO 1199, *Geotrichum fragrans* CBS 164.32, *Geotrichum loubieri* CBS 252.61, *Hanseniaspora guilliermondii* IAM 4972, *Hansenula methanolosa, Hansenula polymorpha* DL1 AKU4752, *Hormoascus philentomus* IFO 1847, *Hormoascus platypodis* IFO 1471, *Hyphopichia burtonii* IFO 0844, *Issatchenkia orientalis* IFO 1279, *Issatchenkia terricola* IFO 0933, *Kluyveromyces lactis* IFO 1012, *Kluyveromyces marxianus* IFO 0541, *Kluyveromyces marxianus* IFO 0288, *Kluyveromyces polysporus* IFO 0996, *Kluyveromyces thermotolerans* IFO 0662, *Komagataella pastoris* IFO 1013, *Lipomyces starkeyi* IFO 0678, *Metschnikowia bicuspidata* IFO 1408, *Metschnikowia pulcherrima* IFO 0561, *Nakazawaea holstii* IFO 0980, *Ogataea minuta* var. *minuta* IFO 0975, *Ogataea pini* IFO 1342, *Ogataea polymorpha* IFO 0799, *Ogataea polymorpha* IFO 1475, *Ogataea wickerhamii* IFO 1706, *Pachysolen tannophilus* IFO 1007, *Pichia canadensis* IFO 0976, *Pichia farinose* IAM 4369, *Pichia jandinii* IFO 0987, *Pichia saitoi* IAM 4945, *Pichia toletana* IFO 0950, *Pichia triangularis* IFO 0836, *Pichia wickerhamii* IFO 1278, *Rhodotorula graminis* IFO 0190, *Rhodotorula minuta* IFO 0387, *Rhodotorula minuta* IFO 0715, *Rhodsporidium diobovatum* IFO 0688, *Rhodsporidium toruloides* IFO 0413, *Saccharomyces bayanus* IFO 0251, *Saccharomyces pastorianus* IFO 1265, *Saccharomyces pastorianus* ATCC 9080, *Saccharomyces rosei* IFO 0252, *Saccharomyces sake, Saccharomyces steineri* IAM 4608, *Saccaromyces unisporus* IFO 0215, *Saccharomycodes ludwigii* IFO 0339, *Saccharomycopsis capsularis* IFO 0672, *Saccharomycopsis malanga* IFO 1710, *Saturnospora dispora* IFO 0035, *Schizoblastosporion kobayasii* IFO 1644, *Schizosaccharomyces pombe* IFO 0347, *Schizosaccharomyces pombe* IFO 0362, *Schwanniomyces occidentalis* var. *occidentalis* IFO 1840, *Sporidiobolus johnsonii* IFO 6903, *Sporobolomyces pararoseus* IFO 0471, *Sporobolomyces salmonicolor* IFO 1038, *Torulaspora delbrueckii* IFO 0381, *Torulopsis methanolevescens, Torulopsis osboenis* IFO 0646, *Torulopsis* sp., *Torulopsis uvae* IFO 0649, *Trichosporon pullulans, Trichosporon* sp. *Trigonopsis variabilis* IFO 0671, *Willopsis saturnus* var. *mrakii* IFO 0895, *Willopsis saturnus* var. *saturnus* IFO 0992, *Yamadazyma farinosa* IFO 0459, *Yamadazyma farinosa* IFO 0602, *Yamadazyma haplophila* IFO 0947, *Zygosaccharomyces naniwensis* IFO 0524, *Zygosaccharomyces* sp. IFO 0522, *Acidiphilium cryptum* IFO 14242, *Aerobacter cloacae* IAM 1221, *Alcaligenes xylosoxidans* IFO 13495, *Alcaligenes xylosoxidans* subsp. *denitrificans* IFO 12669, *Alcaligenes xylosoxidans* subsp. *denitrificans* ATCC 15173, *Arthrobacter globiformis* ATCC 8010, *Arthrobacter protophormiae* IFO 12128, *Aureobacterium esteraromaticum* IFO 3752, *Bacillus badius* IAM 11059, *Bacillus sphaericus* IFO 3525, *Brevibacterium ammomiagenes* IFO 12071, *Buttiauxella agrestis* JCM 1090, *Cedecea davisiae* JCM 1685, *Cellulomonas* sp. JCM 2471, *Cellulomonas turbata* IFO 15015, *Citrobacter freundii* IFO 12681, *Clostridium cylindrosporum* IFO 13695, *Comamonas testosteroni* IFO 12047, *Corynebacterium acectoacidophilum* ATCC 21476, *Corynebacterium ammoniagenes* IFO 12072, *Corynebacterium glutamicum* ATCC 21269, *Corynebacterium glutamicum* ATCC 13287, *Enterobacter aerogenes* IFO 13534, *Enterobacter cloacae* IFO 12935, *Erwinia carotovora* subsp. *carotovora* IFO 3830, *Escherichia coli* IFO 12734, *Flavobacterium flavesceus, Klebsiella planticola* IFO 3317, *Luteococcus japonicus* IFO 12422, *Microbacterium arborescens* IFO 3750, *Micrococcus flavus, Micrococcus luteus* IFO 13867, *Ochrobactrum* sp. IFO 12950, *Proteus inconstans* IFO 12931, *Proteus mirabilis* IFO 3849, *Proteus rettgeri* IFO 1350, *Proteus vulgaris* IFO 3167, *Providencia stuartii* IFO 12930, *Pseudomonas aeruginosa* IAM 1007, *Pseudomonas putida* IFO 14164, *Pseudomonas stutzeri* IFO 13596, *Rhodococcus equi* JCM 1313, *Sarcina lutea, Serratia plymuthicum* IFO 3055, *Serratia proteamaculans* subsp. *proteamaculans* IFO 12979, *Sphingobacterium spiritivorum* JCM 1277, *Tsukamurella paurometabolum* IFO 12160, *Absidia orchidis* HUT 1036, *Acremonium bacillisporum* IFO 9387, *Aegerita candida* IFO 6988, *Agrocybe cylindracea* IFO 30299, *Amylostereum areolatum* IFO 9221, *Aspergillus parasiticus* IFO 4403, *Aspergillus phoenicis* IFO 6670, *Byssochlamys fulva* IFO 6307, *Chaetomidium fimeti* IFO 30419, *Chaetosartorya stromatoides* IFO 9652, *Cladosporium resinae* F. *avellaneum* IFO 6367, *Coprinus cinereus* TD-822, *Coprinus lagopus* IFO 9533, *Coprinus* sp., *Crinipellis stipitaria* IFO 30259, *Endophragmia alternata* IFO 30204, *Flavolus arcularius, Fomitopsis pubertatis, Fusarium merismoides* IFO 30040, *Ganoderma lucidum* IFO 31863, *Glomerella cingu-*

*lata* IFO 5257, *Laetiporus sulphureus, Lentinus lepideus, Lenzites betulina* IFO 8715, *Macrophoma commelinae* IFO 9569, *Monascus purpureus* IFO 5965, *Mortierella isabellina* IFO 7829, *Paecilomyces varioti* HUT 4028, *Penicillium chermesinum* IFO 5800, *Penicillium chrysogenum* IFO 4640, *Penicillium expansum* IFO 5854, *Penicillium lilacinium* IFO 31914, *Phialophora fastigiata* IFO 6850, *Pholiota aurivella* IFO 30265, *Pholiota limonella* IFO 31868, *Pleurotus dryinus, Pleurotus ostreatus, Pleurotus porrigens, Scopulariopsis brevicaulis* IFO 4843, *Sehizophyllum commune* IFO 6503, *Sehizophyllum commune* IFO 6504, *Sporotrichum aurantiacum* IFO 9381, *Zygorhynchus moelleri* HUT 1305, *Microtetraspora roseoviolacea* IFO 14098, *Streptomyces achromogenes* subsp. *rubradiris* IFO 14000, *Streptomyces* sp. and *Streptomyces aureus* NIHJ 122.

These microorganisms can be obtained generally from stock cultures which are readily available at no cost or at cost. These may also be isolated from the natural kingdom. In this connection, these microorganisms may optionally be subjected to induced mutagenesis to obtain strains having characteristics more beneficial to the intended reaction. Furthermore, the strains derived from these microorganisms by genetic engineering or biotechnological processes, such as recombinant DNA technology or cell fusion may also be employed. As an example of such microorganism, there can be mentioned *Escherichia coli* HB101 (pNTCRG) FERM BP-6898 (PCT/JP00/08321) harboring the reductase gene derived from *Candida magnoliae* IFO 0705.

For the cultivation of these microorganisms, any nutrient sources that these microorganisms are generally able to utilize can be employed. For example, as carbon sources, saccharides such as glucose, sucrose, maltose, etc.; organic acids such as lactic acid, acetic acid, citric acid, propionic acid, etc.; alcohols such as ethanol, glycerol, etc.; hydrocarbons inclusive of paraffin; oils such as soybean oil, rapeseed oil, etc.; and mixtures thereof, and as nitrogen sources, ammonium sulfate, ammonium phosphate, urea, yeast extract, meat extract, peptone, corn steep liquor, etc. can be admixed. Furthermore, inorganic salts, vitamins, and other nutrients can also be properly admixed.

The above microorganisms can be cultured under the conventional conditions. For example, they are cultured aerobically under the pH of 4.0 to 9.5 in the temperature range of 20° C. to 45° C. for 10 to 96 hours. To permit a microorganism to act on a dihydroxyoxohexanoic acid monoacyl derivative, usually a culture of the above microorganism can be used as such for the reaction but a concentrate of the culture broth can likewise be employed. Moreover, in cases where some ingredients in the culture broth might adversely affect the reaction, it is preferred to use the cells or processed cells as obtainable by centrifugation and/or other treatments on the culture broth.

The processed cells mentioned above are not particularly restricted but include, for example, dried cells obtainable by dehydration with acetone or diphosphorus pentoxide or by drying with a desiccator or a fan, surfactant-treated cells, an enzymatic digest of cells, immobilized cells, or a cell-free extract obtainable by disruption of cells. Furthermore, from the culture broth, an enzyme catalyzing asymmetric reduction may be purified and used.

In conducting the reduction reaction, the substrate dihydroxyoxohexanoic acid monoacyl derivative can be added all at once in the initial stage of the reaction or serially in portions with the progress of reaction.

The temperature during the reaction is generally 10 to 60° C., preferably 20 to 40° C., and the pH during the reaction is 2.5 to 9, preferably 5 to 9.

The concentration of the microorganism in the reaction mixture can be properly selected according to its ability to reduce the substrate. The concentration of the substrate in the reaction mixture is preferably 0.01 to 50% (w/v), more preferably 0.1 to 30%.

The reaction is usually carried out under shaking or stirring with aeration. The reaction time is properly selected according to the concentration of the substrate, the concentration of the microorganism, and other reaction conditions. Generally, the various conditions are preferably selected so as to insure that the reaction may be completed in 2 to 168 hours.

To promote the reduction reaction, it is preferred to add an energy source, such as glucose, ethanol, and/or the like, in a proportion of 1 to 30% to the reaction mixture, for it will lead to a more satisfactory result. The reaction can also be accelerated by adding a coenzyme, such as reduced nicotinamide-adenine dinucleotide (NADH) or reduced nicotinamide-adenine dinucleotide phosphate (NADPH), which is generally considered to be necessary for reduction reactions by biological techniques. More particularly, these may be directly added to the reaction mixture or a reaction system producing NADH or NADPH may be added together with the oxidized coenzyme to the reaction mixture. For example, the reaction system which reduces NAD to NADH as a formate dehydrogenase produces carbon dioxide and water from formic acid or the reaction system which reduces NAD or NADP to NADH or NADPH respectively, as a glucose dehydrogenase produces gluconolactone from glucose can be exploited. Furthermore, it is also effective to add a surfactant such as Triton (product of Nakalai Tesque), Span (product of Kanto Chemical) or Tween (product of Nakalai Tesque) to the reaction mixture. Moreover, for the purpose of avoiding inhibition of the reaction by the substrate and/or alcohol, which is the byproduct of the reduction reaction, a water-insoluble organic solvent such as ethyl acetate, butyl acetate, isopropyl ether, toluene or the like may be added to the reaction mixture. For the purpose of enhancing the solubility of the substrate, a water-soluble organic solvent, such as methanol, ethanol, acetone, tetrahydrofuran, dimethyl sulfoxide, or the like, may also be added.

The trihydroxyhexanoic acid monoacyl derivative produced by the reduction reaction can be recovered, directly from the reaction mixture or after removal of the cells and others, extraction with a solvent, such as ethyl acetate, toluene, or the like, and subsequent removal of the solvent. Moreover, the trihydroxyhexanoic acid monoacyl derivative can be obtained in a highly pure grade by a purification procedure such as recrystallization, silica gel column chromatography or the like.

Step (4)

In this step, the (3R,5S)-configured trihydroxyhexanoic acid monoacyl derivative represented by the following formula (VI);

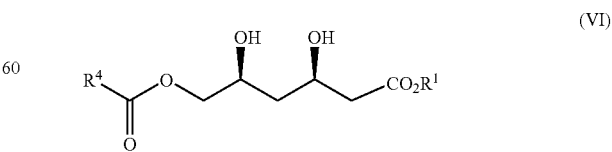

as obtained in the step (3), is treated with an acetal-forming reagent in the presence of an acid catalyst to produce a (4R,6S)-configured acyloxymethyldioxanylacetic acid derivative represented by the following formula (VII);

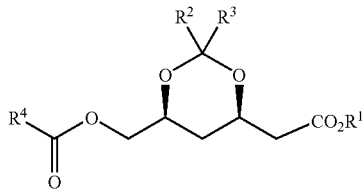

(VII)

In the step (4), the acetal-forming reagent which can be used includes, for example, a ketone, an aldehyde, an alkoxyalkane, and an alkoxyalkene. As specific examples of said ketone, aldehyde, alkoxyalkane and alkoxyalkene, there can be mentioned, for example, acetone, cyclohexanone, formaldehyde, benzaldehyde, dimethoxymethane, 2,2-dimethoxypropane, 2-methoxypropene, and 1,1-dimethoxycyclohexane, etc. The preferred are acetone, 2-methoxypropene, 2,2-dimethoxypropane, etc. and more preferred is 2,2-dimethoxypropane. The level of use of the acetal-forming reagent relative to the trihydroxyhexanoic acid monoacyl derivative is preferably 1 to 10 molar equivalents, more preferably 1 to 5 molar equivalents. For promoting the reaction, the acetal-forming reagent can be used as the reaction solvent as well.

The acid catalyst which can be used in the step (4) includes Lewis acids or Brönsted acids. As said Lewis acids and Brönsted acids, there can be mentioned, for example, Lewis acids such as aluminum trichloride, boron trifluoride, zinc dichloride, tin tetrachloride, etc.; carboxylic acids such as oxalic acid, formic acid, acetic acid, benzoic acid, trifluoroacetic acid, etc.; sulfonic acids such as methanesulfonic acid, benzensulfonic acid, p-toluenesulfonic acid, camphorsulfonic acid, etc.; and inorganic acids such as hydrogen chloride, hydrogen bromide, sulfuric acid, nitric acid, boric acid, etc.

The level of use of the acid catalyst in the step (4), relative to the trihydroxyhexanoic acid monoacyl derivative, is preferably 0.001 to 0.5 molar equivalent, more preferably 0.005 to 0.1 molar equivalent.

The acetal-forming reaction using said acid catalyst is a side reaction involving the intramolecular hydroxyl groups, and it has heretofore been difficult to let the desired reaction proceed with good efficiency. Regarding side reactions, a cyclization reaction involving the intramolecular hydroxyl groups and the ester group, for instance, produces an acyloxymethylhydroxylacetone represented by the following formula (XV);

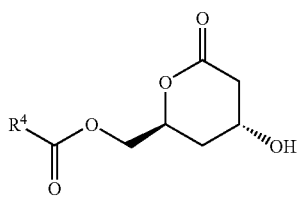

(XV)

(in the formula, $R^4$ is as defined hereinbefore) as a byproduct. When an alkoxyalkane or alkoxyalkene is used as the acetal-forming reagent, the byproduct alcohol reacts with the above compound (XV) to give an analog compound (having different ester group) of said acyloxymethyldiox alylacetic acid derivative represented by the following formula (XIII);

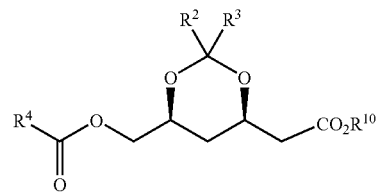

(XIII)

(in the formula, $R^2$, $R^3$ and $R^4$ are as defined hereinbefore; and $R^{10}$ represents a lower alkyl group (preferably containing 1 to 4 carbon atoms) which is different from $R^1$) as a byproduct. When 2,2-dimethoxypropane, for instance, is used as the acetal-forming reagent, the byproduct methanol takes part in the reaction to give an acyloxymethyldioxalylacetic acid methyl ester of the above formula (XIII) in which $R^{10}$ represents a methyl group as a byproduct.

By-production of these impurities detract from the yield and quality of the objective product compound, so that when an acetal-forming reaction is to be conducted using said acid catalyst, the reaction conditions such as reaction temperature, reaction time, amounts of reagents, etc. are necessary to be critically selected and controlled.

The inventors of the present invention developed a method of conducting the acetal-forming reaction in the presence of an amine salt composed of an acid and an amine as a catalyst, whereby the formation of said impurities (XIII) and (XV) and several other trace byproduct impurities, which have not been structurally established, can be suppressed to a minimum without detracting from the yield. As the acid, any of the acids mentioned hereinbefore can be employed, and the preferred include hydrogen chloride, hydrogen bromide, sulfuric acid, trifluoroacetic acid, methanesulfonic acid, benzenesulfonic acid, and p-toluenesulfonic acid. The level of use of the acid relative to the trihydroxyhexanoic acid monoacyl derivative is preferably 0.001 to 0.5 molar equivalent, more preferably 0.005 to 0.1 molar equivalent.

The amine includes ammonia; primary amines such as methylamine, ethylamine, butylamine, aniline, etc.; secondary amines such as diethylamine, diisopropylamine, diphenylamine, piperidine, morpholine, etc.; and tertiary amines such as triethylamine, tributylamine, diisopropylethylamine, N-methylmorpholine, N-methylpiperidine, pyridine, 2-methylpyridine, 3-methylpyridine, imidazole, N,N-dimethylaminopyridine, 1,7-diazabicyclo[5,4,0]-undec-7-ene, and so forth. The preferred are tertiary amines, with triethylamine, N-methylmorpholine, diisopropylethylamine, pyridine, 2-methylpyridine, 3-methylpyridine or imidazole being more preferred. The level of use of the amine relative to the acid is preferably 1 to 10 molar equivalents, more preferably 1 to 3 molar equivalents.

This reaction may be carried out using an amine salt, as a catalyst, prepared from an acid and an amine and isolated in advance. The amine salt includes, for example, pyridinium hydrochloride, pyridinium hydrobromide, pyridinium sulfate, pyridinium trifluoroacetate, pyridinium methanesulfonate, pyridinium p-toluenesulfonate, triethylammonium hydrochloride, triethylammonium sulfate, 3-methylpyridinium p-toluenesulfonate, N-methylmorpholine p-toluenesulfonate salt, N,N-dimethylaminopyridinium benzenesulfonate, diisopropylammonium hydrochloride, ammonium hydrochloride, ammonium sulfate, ammonium nitrate, and ammonium methyl p-toluenesulfonate. The preferred is pyridinium p-toluenesulfonate or triethylammonium p-toluenesulfonate. The level of use of the amine salt relative to the trihydroxyhexanoic acid monoacyl derivative is preferably 0.001 to 0.5 molar equivalent, more preferably 0.005 to 0.1 molar equivalent.

For conducting the reaction according to the step (4), various organic solvents can be used as the reaction solvent. As such organic solvents, there can be mentioned, for example, hydrocarbon solvents such as benzene, toluene, cyclohexane, etc.; ether solvents such as diethyl ether, tetrahydrofuran, 1,4-dioxane, methyl t-butyl ether, dimethoxyethane, etc.; ester solvents such as ethyl acetate, butyl acetate, etc.; ketone solvents such as acetone, methyl ethyl ketone, etc.; halogenated hydrocarbon solvents such as methylene chloride, chloroform, 1,1,1-trichloroethane, etc.; nitrogen-containing solvents such as N,N-dimethylformamide, acetamide, formamide, acetonitrile, etc.; and aprotic polar solvents such as dimethyl sulfoxide, N-methylpyrrolidone, hexamethylphosphoric triamide, etc. These organic solvents can be used each independently or two or more of them may be used in combination. The preferred are toluene, acetone, ethyl acetate, methylene chloride, tetrahydrofuran, methyl tert-butyl ether, dimethylformamide, and acetonitrile, with acetone being more preferred.

The reaction temperature in the step (4) is −20° C. to 100° C., preferably 0° C. to 50° C.

The after-treatment following the step (4) may be carried out by the routine after-treatment for recovery of the product from a reaction mixture. For example, water is added to the reaction mixture after completion of the reaction and the extraction is carried out with an ordinary extractant solvent, for example, ethyl acetate, diethyl ether, methylene chloride, toluene, or hexane. From the extract thus obtained, the reaction solvent and extractant solvent are removed by heating under reduced pressure or the like procedure to give the objective compound.

The objective compound thus obtained tends to contain various impurities originating from various decompositions and side reactions which take place in the course of production. Particularly, it tends to contain at least one member of the group consisting of an acyloxyhydroxylactone represented by the following general formula (XV);

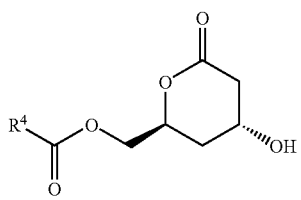

(XV)

(in the formula, $R^4$ is as defined above), an analog compound (having different ester group) of an acyloxymethyldioxalylacetic acid derivative represented by the following general formula (XIII);

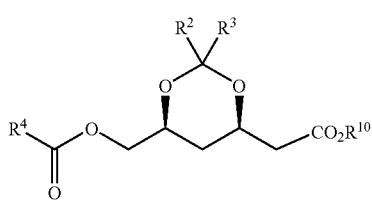

(XIII)

(in the formula, $R^2$, $R^3$ and $R^4$ are respectively as defined above; $R^{10}$ represents a lower alkyl group which is different from $R^1$), a diastereomer represented by the following formula (XIV);

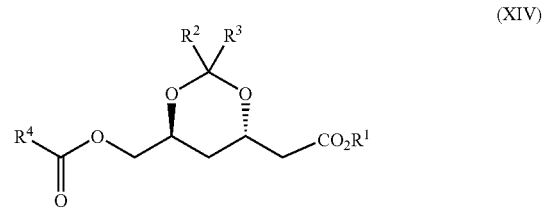

(XIV)

(in the formula, $R^1$, $R^2$, $R^3$ and $R^4$ are respectively as defined above), and the reaction substrate represented by the formula (VI), and in order to obtain the objective compound of high quality, these impurities need to be removed. Generally, however, any impurity structurally resembling the objective compound (structural analog) is not easy to remove, and in order that such impurities may be removed to give the objective compound of high quality, a valid purification/isolation process is required. The inventors of the present invention found that said impurities can be efficiently removed by carrying out a crystallization under the conditions described below.

The crystallization solvent for use in the present invention is preferably an aliphatic hydrocarbon solvent. Specifically, there can be mentioned, for example, aliphatic hydrocarbons of 5 to 20 carbon atoms, such as pentane, petroleum ether, neopentane, hexane, cyclohexane, methylcyclohexane, heptane, cycloheptane, octane, isooctane, nonane, decane, undecane, dodecane, etc. Among these, pentane, hexane, methylcyclohexane, heptane, octane, and isooctane are preferred. These may be used each independently or in a combination of two or more species.

Particularly in terms of removal of the solvent from wet crystals by desiccation or the recovery and reuse of the solvent (distillative recovery), the use of a solvent having a comparatively low boiling point is preferred. As such solvents, there can generally be mentioned solvents having a boiling point of not higher than about 100° C. at atmospheric or subatmospheric pressure. More particularly, for example, aliphatic hydrocarbon solvents of 5 to 8 carbon atoms, such as pentane, hexane, methylcyclohexane, heptane, octane, isooctane, etc. can be mentioned, and when the cost of the solvent, ease of handling, and other factors are globally taken into consideration, hexane and methylcyclohexane are more preferred.

The use of the above aliphatic hydrocarbon solvent provides for the stabilization and assurance of a high yield of the above compound as well as a high degree of purification, that is to say effective removal of various impurities, particularly said compounds (XIII), (XIV), (XV) and (VI). The level of use of said aliphatic hydrocarbon solvent is preferably such that the obtainable product at completion of crystallization of said compound (VII) retains sufficient fluidity, and may, for example, be about 5 to 20 parts by weight, or even more in some cases, relative to said compound (VII).

For the crystallization of said compound (VII) in the present invention, crystallization by cooling, crystallization by concentration, and other processes for crystallization can be used each independently or in combination. The crystallization by concentration, mentioned above, may be a crystallization process in which a solution composed of a solvent other than the aliphatic hydrocarbon solvent is converted to a solution composed of said aliphatic hydrocarbon solvent. Moreover, seed crystals may be added in this crystallization.

In the present invention, for the purpose of improving at least one parameter among the solubility, yield, treatment concentration, purification effect (efficiency of impurity removal), and physical properties of obtainable crystals of the above compound (VII), an auxiliary solvent can be used in addition to said aliphatic hydrocarbon solvent in conducting the crystallization. The above auxiliary solvent may be added to said aliphatic hydrocarbon solvent as necessary or the above compound (VII) may be dissolved in the auxiliary solvent in advance and the solution added to said aliphatic hydrocarbon solvent.

The auxiliary solvent mentioned above is not particularly restricted but includes, for example, acetone, methyl ethyl ketone, tetrahydrofuran, methyl tert-butyl ether, ethyl acetate, isopropanol, tert-butyl acetate, ethanol, isopropyl alcohol, toluene, benzene, xylene, chlorobenzene, methylene chloride, chloroform, and 1,2-dichloroethane, etc. These may be used each independently or in a combination of two or more species. Among these, ethyl acetate, toluene, methyl tert-butyl ether, methylene chloride, etc. contribute to increased solubility and improved treatment effects such as treatment concentration and purification effect.

The auxiliary solvent mentioned above expresses its effect more prominently when used in a suitable amount in combination with said aliphatic hydrocarbon solvent, which suitable amount is established according to the characteristics of auxiliary solvent in relation to the desired effect and other factors. The optimal level of use of said auxiliary solvent can be found by simple experimentation. From the standpoint of yield and purification effect, the level of use of the above auxiliary solvent is preferably such that the weight ratio of said auxiliary solvent and said aliphatic hydrocarbon solvent (auxiliary solvent/aliphatic hydrocarbon solvent) is not greater than 1 at completion of the procedure for crystallization of said compound (VII). The more preferred level is such that said ratio will be 0.5 or less.

The purification/isolation method according to the present invention can be carried out in the neighborhood of room temperature. Where necessary, the method can be practiced under warming or cooling, for example at a temperature not over about 60° C., usually at 50° C. to −30° C.

The above compound (VII) thus obtained can be separated by a solid-liquid separation technique, optionally followed by cake washing and drying. The above solid-liquid separation technique is not particularly restricted but includes, for example, filtration under pressure, suction filtration, centrifugation, and so forth. The above-mentioned drying is preferably carried out under reduced pressure (drying in vacuo) at a temperature not exceeding about 60° C. in order to avoid pyrolysis or fusion.

In the acyloxymethyldioxanylacetic acid derivative of the following formula (VII);

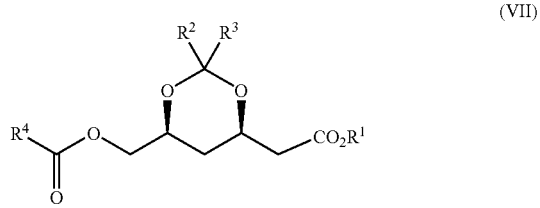

(VII)

as obtained in the step (4), $R^2$ and $R^3$ each independently represents a hydrogen, an alkyl group of 1 to 12 carbon atoms, an aryl group of 6 to 12 carbon atoms, or an aralkyl group of 7 to 12 carbon atoms. Specifically, methyl, ethyl, tert-butyl, hexyl, phenyl, benzyl, p-methoxybenzyl and like groups can be mentioned. The preferred is a methyl group.

Moreover, $R^2$ and $R^3$ may jointly form a ring. For example, $R^2$ and $R^3$ may form a cyclopentane ring, a cyclohexane ring, a cycloheptane ring, a benzocyclopentane ring or the like to thereby constitute a spiro structure with the 1,3-dioxane ring.

Step (5)

In this step, the (4R,6S)-configured acyloxymethyldioxanylacetic acid derivative represented by the following formula (VII);

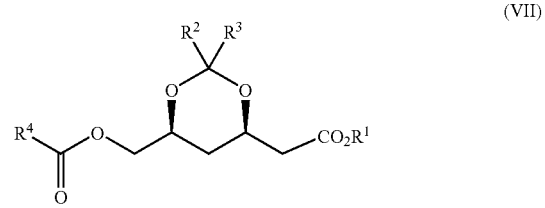

(VII)

as obtained in the step (4), is subjected to solvolysis in the presence of a base by the known method or the like, to give a (4R,6S)-configured hydroxymethyldioxanylacetic acid derivative of the general formula (I);

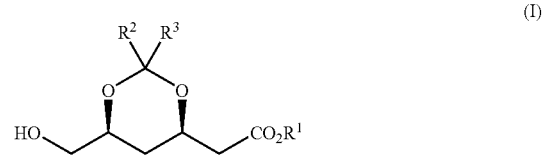

(I)

The base which can be used for the solvolysis in the step (5) includes inorganic and organic bases, such as sodium carbonate, potassium carbonate, sodium hydrogen carbonate, potassium hydrogen carbonate, sodium hydroxide, potassium hydroxide, calcium hydroxide, lithium hydroxide, barium hydroxide, magnesium hydroxide, sodium acetate, potassium acetate, ammonia, triethylamine, pyridine, piperidine, N,N-dimethylaminopyridine, and so forth. The preferred is potassium carbonate.

The level of use of the base in this step, relative to the acyloxymethyldioxanylacetic acid derivative, is 0001 equivalent to 5 equivalents, preferably 0.01 equivalent to 1.0 equivalent.

In step (5), for effecting the solvolysis, the reaction is carried out in water or in a protic organic solvent, or in a mixture of water or a protic organic solvent and an aprotic organic solvent. The protic organic solvent mentioned above includes, for example, alcohol solvents, such as methanol, ethanol, butanol, isopropyl alcohol, ethylene glycol, methoxyethanol, etc.; and amine solvents, such as diethylamine, pyrrolidine, piperidine, and so forth. The aprotic organic solvent mentioned above includes, for example, hydrocarbon solvents such as benzene, toluene, cyclohexane, etc.; ether solvents such as diethyl ether, tetrahydrofuran, 1,4-dioxane, methyl t-butyl ether, dimethoxyethane, etc.; ester solvents such as ethyl acetate, butyl acetate, etc.; ketone solvents such as acetone, methyl ethyl ketone, etc.; halogenated hydrocarbon solvents such as methylene chloride, chloroform, 1,1,1-trichloroethane, etc.; nitrogen-containing solvents such as N,N-dimethylformamide, acetonitrile, etc.; and aprotic polar solvents such as dimethyl sulfoxide, N-methylpyrrolidone, hexamethylphosphoric triamide, and so forth. The preferred are water, methanol, and ethanol.

The reaction temperature for the step (5) is −20° C. to 100° C., preferably −10° C. to 50° C.

The after-treatment following completion of the reaction may be the after-treatment which is generally carried out for recovery of the product from the reaction mixture. For example, the reaction mixture available on completion of the reaction is added with water and extracted with the common extractant solvent, such as ethyl acetate, diethyl ether, methylene chloride, toluene, hexane or the like. From the extract thus obtained, the reaction solvent and extractant solvent are removed by heating under reduced pressure or the like procedure, to isolate the objective compound. As an alternative, after completion of the reaction, the reaction solvent may be immediately distilled off by heating under reduced pressure or the like procedure, and then the same procedure as above be carried out. The objective product thus obtained may be purified to a still higher purity by the routine method such as purification by crystallization, fractional distillation, column chromatography, and/or the like.

BEST MODE FOR CARRYING OUT THE INVENTION

The following examples are intended to illustrate the present invention in further detail without defining the scope of the invention.

EXAMPLE 1

(5S)-5,6-dihydroxy-3-oxohexanoic tert-butyl ester

To 21.3 mL (35 mmol) of a solution of n-butyllithium in hexane (1.5 mol/L) was added a solution of diisopropylamine (3.54 g, 35 mmol)-tetrahydrofuran (10 mL) dropwise under stirring at 5° C., and the mixture was stirred under argon for 1 hour to prepare a lithium diisopropylamide solution. After this solution was cooled to −70° C., 4.06 g (35 mmol) of tert-butyl acetate was added dropwise thereto and the mixture was stirred at the same temperature for 1 hour. Then, 1 mL of a solution of (S)-β-hydroxy-γ-butyrolactone (1.02 g, 10 mmol) in THF was added dropwise and the whole mixture was stirred at −70° C. for 2 hours, at the end of which time the temperature was increased to −10° C. In a separate vessel, 60 mL of 1N-hydrochloric acid and 60 ml of diethyl ether were stirred to mix and the above reaction mixture was poured therein. The aqueous phase was adjusted to pH 6.5 with 1N-hydrochloric acid and, after standing, the organic layer was separated. The aqueous layer was further extracted with 3 portions of ethyl acetate, 50 mL each, and the organic layers were pooled and dehydrated over anhydrous magnesium sulfate. The solvent was then distilled off under reduced pressure and the residue was purified by silica gel column chromatography (Kieselgel 60, product of 1.56 g of (5S)-5,6-dihydroxy-3-oxohexanoic tert-butyl ester (yellow oil) was obtained. Yield: 71%.

$^1$H-NMR (CDCl$_3$, 400 MHz/ppm); 1.48 (9H,s), 2.68–2.83 (2H, m)m, 3.05–3.80 (2H, bs), 3.42 (2H, s), 4.02–4.17 (2H, m), 4.40 (1H, m) $^{13}$C-NMR (CDCl$_3$, 400 MHz/ppm); 27.8, 45.7, 51.0, 65.6, 68.0, 82.3, 166.4, 203.4 IR (neat); 3425, 3000, 1710, 850 cm$^{-1}$ [α]$_D^{20}$=−17.25 (c=2.14, MeOH).

EXAMPLE 2

(5S)-5,6-dihydroxy-3-oxohexanoic tert-butyl ester

To 30 mL (45 mmol) of a solution of n-butyllithium in hexane (1.5 mol/L) was added a solution of diisopropylamine (5.01 g, 49.5 mmol)-tetrahydrofuran (5 mL) dropwise under stirring at 5° C., and the mixture was stirred under argon for 1 hour to prepare a lithium diisopropylamide solution. In a separate vessel, 1.02 g (10 mmol) of (S)-β-hydroxy-γ-butyrolactone and 2.32 g (20 mmol) of tert-butyl acetate were dissolved in 8.0 mL of tetrahydrofuran and the mixture was stirred under argon at 0 to 5° C. To this solution, the lithium diisopropylamide solution prepared above was added dropwise over 30 minutes, and the mixture was further stirred at 5 to 20° C. for 16 hours. In a separate vessel, 35 mL of 3N-hydrochloric acid and 30 ml of ethyl acetate were stirred to mix and the above reaction mixture was poured therein. After standing, the organic layer was taken, washed with saturated aqueous sodium chloride solution, and dehydrated over anhydrous magnesium sulfate. The solvent was then distilled off under reduced pressure and the residue was purified by silica gel column chromatography (Kieselgel 60, product of Merck; hexane:ethyl acetate=2:1) to give 124 mg of (5S)-5,6-dihydroxy-3-oxohexanoic tert-butyl ester (yellow oil). Yield 6%.

EXAMPLE 3

(5S)-5,6-dihydroxy-3-oxohexanoic tert-butyl ester

To 22.9 mL (35 mmol) of a solution of n-butyllithium in hexane (1.5 mol/L) was added a solution of diisopropylamine (3.90 g, 38.5 mmol)-tetrahydrofuran (3 mL) dropwise under stirring at 5° C., and the mixture was stirred under argon for 1 hour to prepare a lithium diisopropylamide solution. In a separate vessel, 1.02 g (10 mmol) of (S)-β-hydroxy-γ-butyrolactone and 2.32 g (20 mmol) of tert-butyl acetate were dissolved in 3.0 mL of tetrahydrofuran and the mixture was stirred under argon at 0 to 5° C. To this solution, 5.7 g (10 mmol) of a solution (1.75 mol/kg) of tert-butylmagnesium chloride in toluene/tetrahydrofuran (1:2.5 by weight) was added dropwise over 10 minutes, and the mixture was further stirred at 5° C. for 50 minutes. To this mixture was added the above-prepared lithium diisopropylamide solution dropwise over 30 minutes, followed by 16 hours of stirring at 5 to 20° C.

In a separate vessel, 30 mL of 3N-hydrochloric acid and 30 ml of ethyl acetate were stirred to mix and the above reaction mixture was poured therein. After standing, the organic layer was taken, washed with saturated aqueous sodium chloride solution, and dehydrated over anhydrous magnesium sulfate. The solvent was then distilled off under reduced pressure and the residue was purified by silica gel column chromatography (Kieselgel 60, product of Merck; hexane:ethyl acetate=2:1) to give 980 mg of (5S)-5,6-dihydroxy-3-oxohexanoic tert-butyl ester (red oil). Yield 48%.

EXAMPLE 4

(5S)-5,6-dihydroxy-3-oxohexanoic tert-butyl ester

To a suspension of 9.82 g (150 mmol) of zinc dust in 40 mL of tetrahydrofuran was added 1.9 mL (15 mmol) of trimethylsilyl chloride at room temperature, and the mixture was stirred for 30 minutes. To this mixture were added 2.4 mL (10.5 mmol) of tert-butyl α-bromoacetate and 4.27 g (42 mmol) of (S)-β-hydroxy-γ-butyrolactone, and the temperature was increased to 65° C. At the same temperature, 15.3 mL (94.5 mmol) of tert-butyl α-bromoacetate was further added gradually over 30 minutes. After completion of addition, the mixture was further stirred at 65° C. for 30 minutes, at the end of which time the reaction mixture was cooled to room temperature and diluted with 50 mL of water. The reaction mixture was then adjusted to pH 6.8 with 20% aqueous NaOH solution and the precipitated solid was filtered off. The filtrate was extracted with 3 portions of ethyl acetate, 100 mL each, and the organic layers were combined and dehydrated over anhydrous sodium sulfate. The solvent was then distilled off under reduced pressure to give a yellow oil. This residue was purified by silica gel column chromatography (Kieselgel 60, product of Merck; hexane: acetone=5:1) to give 2.66 g of (5S)-5,6-dihydroxy-3-oxohexanoic tert-butyl ester (yellow oil). Yield 29%.

EXAMPLE 5

(5S)-6-benzoyloxy-5-hydroxy-3-oxohexanoic tert-butyl ester

To a solution of 16.8 g (77 mmol) of the (5S)-5,6-dihydroxy-3-oxohexanoic tert-butyl ester produced in Example 1 in 120 mL of methylene chloride were added 11.2 mL of pyridine and 10.2 mL of benzoyl chloride at 0° C., and the mixture was stirred at 0° C. for 2 hours. After completion of the reaction, the reaction mixture was diluted with 38 mL of water and adjusted to pH 7 with 20% aqueous NaOH solution. The aqueous layer was separated and further extracted with 2 portions of methylene chloride, 120 mL each. The organic layers were combined and dehydrated over anhydrous sodium sulfate and the solvent was distilled off under reduced pressure to give an oil. This residue was purified by silica gel column chromatography (Kieselgel 60, product of Merck; hexane:acetone=5:1) to give 19.3 g of (5S)-6-benzoyloxy-5-hydroxy-3-oxohexanoic tert-butyl ester (white solid).

Yield 78%. $^1$H-NMR (CDCl$_3$, 400 MHz/ppm); 1.46 (9H, s), 2.85 (2H, d), 3.09 (1H, d), 3.42 (2H, s), 4.36 (2H, m), 4.50 (1H, m), 7.45 (2H, dd), 7.56 (1H, dd), 8.05 (2H, d) IR (KBr); 3495, 1730, 1700, 1335, 1290, 1150, 720 cm$^{-1}$ m.p. 67 to 68° C.

EXAMPLE 6

(5S)-6-benzoyloxy-5-hydroxy-3-oxohexanoic tert-butyl ester

To 109 mL (175 mmol) of a solution of n-butyllithium in hexane (1.5 mol/L) was added a solution of diisopropylamine (19.48 g, 195 mmol)-tetrahydrofuran (30 mL) dropwise under stirring at 5° C., and the mixture was stirred under argon for 1 hour to prepare a lithium diisopropylamide solution. In a separate vessel, 5.10 g (50 mmol) of (S)-β-hydroxy-γ-butyrolactone and 14.5 g (125 mmol) of tert-butyl acetate were dissolved in 60 ml of tetrahydrofuran and the solution was stirred under argon at 0 to 5° C. To this solution, 27.8 g (50 mmol) of a mixed solution of tert-butylmagnesium chloride in toluene/tetrahydrofuran (1:2.5, by weight) (1.8 mol/kg) was added dropwise over 30 minutes and the mixture was further stirred at 5° C. for 30 minutes. To this mixture was added the above-prepared lithium diisopropylamide solution dropwise over 3 hours, and the mixture was further stirred at 5 to 20° C. for 16 hours. In a separate vessel, 25.05 g of acetic acid, 75 mL of water, and 150 mL of ethyl acetate were stirred to mix and the above reaction mixture was poured therein. After standing, the aqueous layer was separated and further extracted with 2 portions of ethyl acetate, 150 mL each. The organic layers were combined, diluted with 20 mL of saturated aqueous sodium chloride solution, and adjusted to pH 3 with 3N-hydrochloric acid. After the aqueous layer was separated, the organic layer was further washed with 20 mL of saturated aqueous sodium hydrogen carbonate solution and dehydrated over anhydrous magnesium sulfate. The solvent was distilled off under reduced pressure to give 18.18 g of a yellow oil containing (5S)-5,6-dihydroxy-3-oxohexanoic tert-butyl ester.

To the above oil, 6.32 g (80 mmol) of pyridine and 50 mL of toluene were added, and the mixture was cooled to 5° C. To this mixture was added 6.32 g (45 mmol) of benzoyl chloride, and the whole mixture was stirred at 5° C. for 1.5 hours. Then, 25 mL of water and 15 mL of 3N-hydrochloric acid were added. This mixture was extracted with 100 mL of ethyl acetate and the organic layer was washed with 30 mL of saturated sodium hydrogen carbonate solution and 50 mL of water twice. The solvent was then distilled off under reduced pressure to give 18.43 g of a yellow oil. This oil was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The analysis showed that the reaction yield of (5S)-6-benzoyloxy-5-hydroxy-3-oxohexanoic tert-butyl ester was 55%.

EXAMPLE 7

(5S)-6-benzoyloxy-5-hydroxy-3-oxohexanoic tert-butyl ester

To 125 mL (225 mmol) of a solution of n-butylmagnesium chloride in tetrahydrofuran (1.8 mol/L) was added 25.04 g (247.5 mmol) of diisopropylamine dropwise under stirring at 40° C., and the mixture was further stirred under argon at 40° C. for 2 hours to prepare a white slurry of chloromagnesium diisopropylamide. In a separate vessel, 5.10 g (50 mmol) of (S)-β-hydroxy-γ-butyrolactone and 1.45 g (125 mmol) of tert-butyl acetate were dissolved in 30 mL of dimethoxyethane and the solution was stirred at 0 to 5° C. under argon. To this solution was added the above-prepared chloromagnesium diisopropylamide slurry dropwise over 3 hours, and the mixture was further stirred at 5 to 20° C. for 16 hours.

In a separate vessel, 28.4 g of acetic acid, 100 mL of water, and 150 ml of ethyl acetate were stirred to mix and the above reaction mixture was poured therein. After standing, the aqueous layer was separated and further extracted with 2 portions of ethyl acetate, 150 ml each. The organic layers were combined, diluted with 20 mL of saturated aqueous sodium chloride solution, adjusted to pH 3 with 3N-hydrochloric acid, and the aqueous layer was separated. The organic layer was further washed with 20 mL of saturated aqueous sodium hydrogen carbonate solution and dehydrated over anhydrous magnesium sulfate, and the solvent was distilled off under reduced pressure to give 14.24 g of a red oil containing (5S)-5,6-dihydroxy-3-oxohexanoic tert-butyl ester. To the above oil, 6.32 g (80 mmol) of pyridine and 50 mL of toluene were added, and the mixture was cooled to 5° C. To this mixture was added 5.62 g (40 mmol) of benzoyl chloride, and the whole mixture was stirred at 5° C. for 1 hour. Then, 25 mL of water and 15 mL of 3N-hydrochloric acid were added. This mixture was extracted with 150 mL of ethyl acetate and the organic layer was washed with 30 mL of saturated sodium hydrogen carbonate solution and 30 mL of water twice. The solvent was then distilled off under reduced pressure to give 18.12 g of a yellow oil. This oil was analyzed by high-performance liquid chromatography (column: Develosil ODS-HG-3 4.6× 250 mm, product of Nomura Chemical, eluent: water/acetonitrile=50/50, flow rate: 1.0 mL/min, detector: UV 220 nm, column temperature: 40° C.). As a result, the reaction yield of (5S)-6-benzoyloxy-5-hydroxy-3-oxohexanoic tert-butyl ester was found to be 53%.

EXAMPLE 8

(5S)-6-benzoyloxy-5-hydroxy-3-oxohexanoic tert-butyl ester

To 141 mL (225 mmol) of a solution of n-butyllithium in hexane (1.6 mol/L) was added a solution of diisopropylamine (25.04 g, 247.5 mmol)-tetrahydrofuran (30 mL) dropwise under stirring at 5° C., and the mixture was stirred under argon for 1 hour to prepare a lithium diisopropylamide solution. In a separate vessel, 5.10 g (50 mmol) of (S)-β-hydroxy-γ-butyrolactone, 14.5 g (125 mmol) of tert-butyl acetate and 9.52 g (100 mmol) of anhydrous magnesium chloride were dissolved in 30 ml of tetrahydrofuran and the solution was stirred under argon at 0 to 5° C. To this solution was added the above-prepared a lithium diisopropylamide solution dropwise over 3 hours, and the mixture was further stirred at 5 to 20° C. for 16 hours. In a separate vessel, 28.4 g of acetic acid, 100 mL of water, and 150 mL of ethyl acetate were stirred to mix and the above reaction mixture was poured therein. After standing, the aqueous layer was separated and further extracted with 2 portions of ethyl acetate, 150 ml each. The organic layers were combined, diluted with 20 mL of saturated aqueous sodium chloride solution, adjusted to pH 3 with 3N-hydrochloric acid, and the aqueous layer was separated. The organic layer was further washed with 20 mL of saturated aqueous sodium hydrogen carbonate solution and dehydrated over anhydrous magnesium sulfate, and the solvent was distilled off under reduced pressure to give 12.74 g of a red oil containing (5S)-5,6-dihydroxy-3-oxohexanoic tert-butyl ester.

To the above oil, 6.32 g (80 mmol) of pyridine and 50 mL of toluene were added, and the mixture was cooled to 5° C. To this mixture was added 5.62 g (40 mmol) of benzoyl chloride, and the whole mixture was stirred at 5° C. for 1 hour. Then, 25 mL of water and 15 mL of 3N-hydrochloric acid were added. This mixture was extracted with 150 mL of ethyl acetate and the organic layer was washed with 30 mL of saturated sodium hydrogen carbonate solution and 30 mL of water twice. The solvent was then distilled off under reduced pressure to give 17.92 g of a red oil. This oil was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). As a result, the reaction yield of (5S)-6-benzoyloxy-5-hydroxy-3-oxohexanoic tert-butyl ester was found to be 55%.

EXAMPLE 9

Purification of (5S)-6-benzoyloxy-5-hydroxy-3-oxohexanoic tert-butyl ester

The oil containing (5S)-6-benzoyloxy-5-hydroxy-3-oxohexanoic tert-butyl ester as produced in Example 6 was analyzed high-performance liquid chromatography (the conditions are described in Example 6). Purity: 48.2 weight % (58.1 area %). As an impurity, the oil contained 4.8 weight % (6.5 area %) of (5S)-5,6-dibenzyloxy-3-oxohexanoic tert-butyl ester. To 18.43 g of this oil ((5S)-6-benzoyloxy-5-hydroxy-3-oxohexanoic tert-butyl ester: 8.88 g) was added 30 mL of toluene to make a homogeneous solution, followed by addition of 80 mL of hexane, and the mixture was cooled to 5° C. (treatment concentration: 8% (substrate weight/solution volume)). To this opaque solution, about 10 mg of seed crystals were added, and the mixture was further stirred vigorously at the same temperature for 1 hour. The resulting crystals were collected by suction filtration, drained thoroughly, washed with 50 mL of hexane, and dried in vacuo (ca 1–5 mmHg, 20 to 40° C., 2 hours), whereby 6.12 g of (5S)-6-benzoyloxy-5-hydroxy-3-oxohexanoic tert-butyl ester was obtained as crystals (crystallization recovery rate 67%). Analysis: purity 97.7 weight % (95.4 area %); (5S)-5,6-dibenzyloxy-3-oxohexanoic tert-butyl ester content: 0.7 weight % (0.7 area %).

EXAMPLE 10

Purification of (5S)-6-benzoyloxy-5-hydroxy-3-oxohexanoic tert-butyl ester

The oil containing (5S)-6-benzoyloxy-5-hydroxy-3-oxohexanoic tert-butyl ester as produced in Example 7 was analyzed by high-performance column chromatography (the conditions are described in Example 6). The purity was 45.0 weight % (47.2 area %) and the impurity (5S)-5,6-dibenzyloxy-3-oxohexanoic tert-butyl ester content: 4.7 weight % (4.9 area %). To 18.12 g of this oil ((5S)-6-benzoyloxy-5-hydroxy-3-oxohexanoic tert-butyl ester: 8.15 g) was added 20 mL of toluene to prepare a homogeneous solution. To this solution was added 80 mL of hexane, and the mixture was cooled to −30° C. (treatment concentration: 8% (substrate weight/solution volume)). To the resulting opaque solution was added about 10 mg of seed crystals, and the mixture was stirred vigorously at the same temperature for 1 hour. The crystals separating out were collected by suction filtration, drained thoroughly, and washed with 50 mL of hexane. This crystal crop was dried in vacuo (ca 1 to 5 mmHg, 20 to 40° C., 2 hours) to obtain 6.68 g of (5S)-6-benzoyloxy-5-hydroxy-3-oxohexanoic tert-butyl ester crystals (crystallization recovery rate 77%). Analysis of the crystals showed a purity of 95.8 weight % (94.9 area %) and a (5S)-5,6-dibenzyloxy-3-oxohexanoic tert-butyl ester content of 1.6 weight % (1.6 area %).

EXAMPLE 11

(3R,5S)-6-benzoyloxy-3,5-dihydroxyhexanoic tert-butyl ester

A large test tube was charged with 5 ml of Medium A described hereinbefore and, after sterilization, inoculated with one of the microorganisms indicated in Table 1 and Table 2. Aerobic shake culture was carried out at 27° C. for 2 to 3 days. From a 1.5 ml portion of the resulting culture, the cells were harvested by centrifugation and suspended in 0.5 ml of 100 mM phosphate buffer (pH 6.5) containing 0.05% of (5S)-6-benzoyloxy-5-hydroxy-3-oxohexanoic tert-butyl ester and 8% of glucose. The suspension was put in a test tube equipped with a threaded stopper and the reaction was carried out under shaking at 27° C. for 20 hours. After the reaction, 4 volumes of ethyl acetate were added to the reaction mixture and after thorough mixing, the cells were centrifugally removed. The supernatant was analyzed by high-performance liquid chromatography for the amount of (3R,5S)-6-benzoyloxy-3,5-dihydroxyhexanoic tert-butyl ester produced per ml of the reaction mixture and the diastereomer ratio (=(3R,5S)/(3S,5S) ratio). The results are shown in Table 1 and Table 2.

TABLE 1

| Microorganism | | | Output (ug/ml) | D.E. (%) |
|---|---|---|---|---|
| Ashbya | gossypii | IFO 0560 | 500.0 | 61.1 |
| Botryoascus | synnaedendrus | IFO 1604 | 330.6 | 63.7 |
| Brettanomyces | custersianus | IFO 1585 | 59.7 | 95.1 |
| Candida | arborea | IAM 4147 | 77.3 | 72.4 |
| Candida | catenulata | IFO 0745 | 46.5 | 10.1 |
| Candida | fennica | CBS 6028 | 135.1 | 87.8 |
| Candida | galacta | IFO 10031 | 121.0 | 84.3 |
| Candida | haemulonii | IFO 10001 | 133.7 | 94.3 |
| Candida | magnoliae | IFO 0705 | 175.0 | 27.1 |
| Candida | musae | IFO 1582 | 39.8 | 33.5 |
| Candida | nitratophila | IFO 10004 | 20.1 | 48.3 |
| Candida | parapsilosis | IFO 0585 | 118.4 | 65.7 |
| Candida | pararugosa | IFO 0966 | 26.6 | 56.0 |
| Candida | stellata | IFO 0701 | 27.4 | 100.0 |
| Citeromyces | matritensis | IFO 0651 | 446.9 | 26.2 |
| Clavispora | lusitaniae | IFO 1019 | 342.1 | 53.7 |
| Cryptococcus | laurentii | IFO 0609 | 37.5 | 14.5 |
| Debaryomyces | carsonii | IFO 0795 | 449.1 | 97.3 |
| Debaryomyces | hansenii var. fabryi | IFO 0794 | 55.4 | 78.8 |
| Debaryomyces | hansenii var. hansenii | IFO 0032 | 130.1 | 93.6 |
| Debaryomyces | hansenii var. hansenii | IFO 0047 | 135.4 | 95.4 |
| Debaryomyces | hansenii var. hansenii | IFO 0018 | 103.1 | 95.5 |
| Debaryomyces | kloeckeri | | 140.7 | 95.4 |
| Debaryomyces | marama | IFO 0668 | 161.5 | 95.4 |
| Debaryomyces | pseudopolymorphus | IFO 1026 | 75.4 | 90.9 |
| Debaryomyces | robertsiae | IFO 1277 | 278.7 | 66.1 |
| Debaryomyces | sp. | IFO 0025 | 32.7 | 74.7 |
| Dekkera | anomala | IFO 0627 | 115.8 | 94.9 |
| Dipodascus | armillariae | IFO 0102 | 154.6 | 76.8 |
| Dipodascus | ovetensis | IFO 1201 | 134.9 | 96.9 |

TABLE 1-continued

| Microorganism | | | Output (ug/ml) | D.E. (%) |
|---|---|---|---|---|
| Dipodascus | tetrasperma | CBS 765.70 | 203.0 | 33.1 |
| Galactomyces | reessii | CBS 179.60 | 378.8 | 25.0 |
| Geotrichum | candidum | CBS 187.67 | 148.6 | 51.8 |
| Geotrichum | fermentans | IFO 1199 | 98.4 | 93.9 |
| Geotrichum | fragrans | CBS 164.32 | 29.1 | 94.1 |
| Geotrichum | loubieri | CBS 252.61 | 81.4 | 14.8 |
| Hanseniaspora | guilliermondii | IAM 4972 | 35.8 | 4.0 |
| Hansenula | methanolosa | | 93.7 | 99.2 |
| Hansenula | polymorpha DL1 | AKU 4752 | 21.6 | 100.0 |
| Hormoascus | philentomus | IFO 1847 | 176.6 | 84.2 |
| Hormoascus | platypodis | IFO 1471 | 260.8 | 36.6 |
| Hyphopichia | burtonii | IFO 0844 | 228.8 | 77.7 |
| Issatchenkia | orientalis | IFO 1279 | 443.0 | 36.4 |
| Issatchenkia | terricola | IFO 0933 | 258.4 | 100.0 |
| Kluyveromyces | lactis | IFO 1012 | 324.6 | 48.8 |
| Kluyveromyces | marxianus | IFO 0541 | 102.7 | 85.9 |
| Kluyveromyces | marxianus | IFO 0288 | 419.3 | 27.1 |
| Kluyveromyces | polysporus | IFO 0996 | 132.6 | 5.1 |
| Kluyveromyces | thermotolerans | IFO 0662 | 500.0 | 100.0 |
| Komagataella | pastoris | IFO 1013 | 246.0 | 66.4 |
| Lipomyces | starkcyi | IFO 0678 | 28.6 | 100.0 |
| Metschnikowia | bicuspidata | IFO 1408 | 381.0 | 39.6 |
| Metschnikowia | pulcherrima | IFO 0561 | 359.4 | 48.0 |

TABLE 2

| Microorganism | | | Output (ug/ml) | D.E. (%) |
|---|---|---|---|---|
| Nakazawaea | holstii | IFO 0980 | 0.5 | 100.0 |
| Ogataea | minuta var. minuta | IFO 0975 | 18.2 | 9.4 |
| Ogataea | pini | IFO 1342 | 268.3 | 43.1 |
| Ogataea | polymorpha | IFO 0799 | 500.0 | 67.3 |
| Ogataea | polymorpha | IFO 1475 | 275.0 | 6.0 |
| Ogataea | wickerhamii | IFO 1706 | 144.8 | 73.6 |
| Pachysolen | tannophilus | IFO 1007 | 488.2 | 5.4 |
| Pichia | canadensis | IFO 0976 | 17.5 | 86.9 |
| Pichia | farinosa | IAM 4369 | 208.9 | 71.4 |
| Pichia | jandinii | IFO 0987 | 296.4 | 96.9 |
| Pichia | saitoi | IAM 4945 | 97.4 | 22.5 |
| Pichia | toletana | IFO 0950 | 300.0 | 13.1 |
| Pichia | triangularis | IFO 0836 | 328.8 | 24.6 |
| Pichia | wickerhamii | IFO 1278 | 175.8 | 81.7 |
| Rhodotorula | graminis | IFO 0190 | 96.5 | 3.3 |
| Rhodotorula | minuta | IFO 0387 | 108.3 | 12.0 |
| Rhodotorula | minuta | IFO 0715 | 0.5 | 100.0 |
| Rhodsporidium | diobovatum | IFO 0688 | 1.8 | 17.4 |
| Rhodsporidium | toruloides | IFO 0413 | 10.2 | 46.7 |
| Saccharomyces | bayanus | IFO 0251 | 375.2 | 18.3 |
| Saccharomyces | pastorianus | IFO 1265 | 442.5 | 80.5 |
| Saccharomyces | pastorianus | ATCC 9080 | 83.1 | 72.9 |
| Saccharomyces | rosei | IFO 0252 | 456.8 | 83.1 |
| Saccharomyces | sake | | 349.5 | 92.6 |
| Saccharomyces | steineri | IAM 4608 | 98.3 | 100.0 |
| Saccharomyces | unisporus | IFO 0215 | 97.0 | 84.5 |
| Saccharomycodes | ludwigii | IFO 0339 | 99.0 | 43.8 |
| Saccharomycopsis | capsularis | IFO 0672 | 112.5 | 76.8 |
| Saccharomycopsis | malanga | IFO 1710 | 0.3 | 100.0 |

TABLE 2-continued

| Microorganism | | | Output (ug/ml) | D.E. (%) |
|---|---|---|---|---|
| *Saturnospora* | *dispora* | IFO 0035 | 16.6 | 16.8 |
| *Schizoblastosporion* | *kobayasii* | IFO 1644 | 207.0 | 54.6 |
| *Schizosaccharomyces* | *pombe* | IFO 0347 | 119.5 | 55.2 |
| *Schizosaccharomyces* | *pombe* | IFO 0362 | 96.3 | 56.0 |
| *Schwanniomyces* | *occidentalis* var. *occidentalis* | IFO 1840 | 219.7 | 46.9 |
| *Sporidiobolus* | *johnsonii* | IFO 6903 | 2.7 | 100.0 |
| *Sporobolomyces* | *pararoseus* | IFO 0471 | 66.0 | 67.8 |
| *Sporobolomyces* | *salmonicolor* | IFO 1038 | 8.8 | 100.0 |
| *Torulaspora* | *delbrueckii* | IFO 0381 | 186.4 | 95.9 |
| *Torulopsis* | *methanolcycscens* | | 337.0 | 33.2 |
| *Torulopsis* | *osboenis* | IFO 0646 | 58.5 | 16.9 |
| *Torulopsis* | sp. | | 99.7 | 84.9 |
| *Torulopsis* | *uvae* | IFO 0649 | 287.1 | 88.8 |
| *Trichosporon* | *pullulans* | | 20.9 | 51.0 |
| *Trichosporon* | sp. | | 4.6 | 19.2 |
| *Trigonopsis* | *variabilis* | IFO 0671 | 126.4 | 13.4 |
| *Willopsis* | *saturnus* var. *mrakii* | IFO 0895 | 445.3 | 3.6 |
| *Willopsis* | *saturnus* var. *saturnus* | IFO 0992 | 394.4 | 6.1 |
| *Yamadazyma* | *farinosa* | IFO 0459 | 472.7 | 86.7 |
| *Yamadazyma* | *farinosa* | IFO 0602 | 97.0 | 55.0 |
| *Yamadazyma* | *haplophila* | IFO 0947 | 7.2 | 66.4 |
| *Zygosaccharomyces* | *naniwensis* | IFO 0524 | 263.1 | 43.0 |
| *Zygosaccharomyces* | sp. | IFO 0522 | 282.8 | 9.4 |

EXAMPLE 12

(3R,5S)-6-benzoyloxy-3,5-dihydroxyhexanoic tert-butyl ester

Using 5 ml of Medium B described hereinbefore, the microorganisms indicated in Table 3 were cultured in the same manner as in Example 11. Thereafter, the reaction was carried out in the same manner. The results are shown in Table 3.

TABLE 3

| Microorganism | | | Output (ug/ml) | D.E. (%) |
|---|---|---|---|---|
| *Acidiphilium* | *cryptum* | IFO 14242 | 2.7 | 12.2 |
| *Aerobacter* | *cloacae* | IAM 1221 | 29.2 | 79.0 |
| *Alcaligenes* | *xylosoxidans* | IFO 13495 | 13.2 | 38.9 |
| *Alcaligenes* | *xylosoxidans* subsp. *denitrificans* | IFO 12669 | 3.9 | 22.9 |
| *Alcaligenes* | *xylosoxidans* subsp. *denitrificans* | ATCC 15173 | 11.2 | 90.3 |
| *Arthrobacter* | *globiformis* | ATCC 8010 | 0.4 | 100.0 |
| *Arthrobacter* | *protophormiae* | IFO 12128 | 28.1 | 100.0 |
| *Aureobacterium* | *esteraromaticum* | IFO 3752 | 245.9 | 24.1 |
| *Bacillus* | *badius* | IAM 11059 | 0.3 | 100.0 |
| *Bacillus* | *sphaericus* | IFO 3525 | 0.7 | 20.2 |
| *Brevibacterium* | *ammoniagenes* | IFO 12071 | 193.1 | 98.8 |
| *Buttiauxella* | *agrestis* | JCM 1090 | 25.7 | 40.3 |
| *Cedecea* | *davisiae* | JCM 1685 | 3.2 | 37.0 |
| *Cellulomonas* | sp. | JCM 2471 | 119.8 | 95.9 |
| *Cellulomonas* | *turbata* | IFO 15015 | 88.8 | 24.3 |
| *Citrobacter* | *freundii* | IFO 12681 | 75.2 | 68.9 |
| *Clostridium* | *cylindrosporum* | IFO 13695 | 4.8 | 50.6 |
| *Comamonas* | *testosteroni* | IFO 12047 | 1.1 | 48.8 |
| *Corynebacterium* | *acectoacidophilum* | ATCC 21476 | 211.3 | 63.4 |
| *Corynebacterium* | *ammoniagenes* | IFO 12072 | 1.8 | 66.0 |
| *Corynebacterium* | *glutamicum* | ATCC 21269 | 269.3 | 92.2 |
| *Corynebacterium* | *glutamicus* | ATCC 13287 | 276.9 | 98.3 |
| *Enterobacter* | *aerogenes* | IFO 13534 | 54.5 | 91.4 |
| *Enterobacter* | *cloacae* | IFO 12935 | 490.7 | 88.9 |
| *Erwinia* | *carotovora* subsp. *carotovora* | IFO 3830 | 1.1 | 100.0 |
| *Escherichia* | *coli* | IFO 12734 | 23.2 | 53.9 |
| *Flavobacterium* | *flavesceus* | | 17.3 | 25.1 |
| *Klebsiella* | *planticola* | IFO 3317 | 127.3 | 61.6 |
| *Luteococcus* | *japonicus* | IFO 12422 | 0.2 | 100.0 |
| *Microbacterium* | *arborescens* | IFO 3750 | 7.6 | 90.8 |

TABLE 3-continued

| Microorganism | | | Output (ug/ml) | D.E. (%) |
|---|---|---|---|---|
| Micrococcus | flavus | | 4.0 | 30.7 |
| Micrococcus | luteus | IFO 13867 | 500.0 | 13.5 |
| Ochrobactrum | sp. | IFO 12950 | 12.5 | 51.4 |
| Proteus | inconstans | IFO 12931 | 5.6 | 87.6 |
| Proteus | mirabilis | IFO 3849 | 1.1 | 100.0 |
| Proteus | rettgeri | IFO 13501 | 0.3 | 100.0 |
| Proteus | vulgaris | IFO 3167 | 0.5 | 100.0 |
| Providencia | stuartii | IFO 12930 | 2.9 | 76.9 |
| Pseudomonas | aeruginosa | IAM 1007 | 2.8 | 100.0 |
| Pseudomonas | putida | IFO 14164 | 11.2 | 31.1 |
| Pseudomonas | stutzeri | IFO 13596 | 8.0 | 32.5 |
| Rhodococcus | equi | JCM 1313 | 48.4 | 72.7 |
| Sarcina | lutea | | 369.2 | 86.8 |
| Serratia | plymuthicum | IFO 3055 | 2.7 | 100.0 |
| Serratia | proteamaculans subsp. proteamaculans | IFO 12979 | 38.5 | 47.3 |
| Sphingobacterium | spiritivorum | JCM 1277 | 61.9 | 33.6 |
| Tsukamurella | paurometabolum | IFO 12160 | 40.6 | 8.2 |

EXAMPLE 13

(3R,5S)-6-benzoyloxy-3,5-dihydroxyhexanoic tert-butyl ester

Using 5 ml of Medium C described hereinbefore, the microorganisms indicated in Table 4 were cultured in the same manner as in Example 11. From 5 ml of each culture, the cells were centrifugally harvested, suspended in 0.5 ml of 100 mM phosphate buffer (pH 6.5) containing 0.05% of (5S)-6-benzoyloxy-5-hydroxy-3-oxohexanoic tert-butyl ester and 8% of glucose, and the reaction was carried out in the same manner. The results are shown in Table 4.

TABLE 4

| Microorganism | | | Output (ug/ml) | D.E. (%) |
|---|---|---|---|---|
| Absidia | orchidis | HUT 1036 | 4.4 | 25.2 |
| Acremonium | bacillisporum | IFO 9387 | 1.0 | 100.0 |
| Aegerita | candida | IFO 6988 | 500.0 | 92.8 |
| Agrocybe | cylindracea | IFO 30299 | 96.2 | 59.5 |
| Amylostereum | areolatum | IFO 9221 | 71.7 | 32.9 |
| Aspergillus | parasiticus | IFO 4403 | 2.6 | 100.0 |
| Aspergillus | phoenicis | IFO 6670 | 1.4 | 32.0 |
| Byssochlamys | fulva | IFO 6307 | 164.6 | 99.2 |
| Chaetomidium | fimeti | IFO 30419 | 0.5 | 100.0 |
| Chaetosartorya | stromatoides | IFO 9652 | 1.6 | 100.0 |
| Cladosporium | resinae F. avellaneum | IFO 6367 | 1.4 | 100.0 |
| Coprinus | cinereus | | 401.3 | 76.0 |
| Coprinus | lagopus | IFO 9533 | 37.9 | 93.7 |
| Coprinus | sp. | | 1.9 | 100.0 |
| Crinipellis | stipitaria | IFO 30259 | 16.6 | 40.6 |
| Endophragmia | alternata | IFO 30204 | 10.4 | 54.9 |
| Flavolus | arcularius | | 217.0 | 8.8 |
| Fomitopsis | pubertatis | | 102.0 | 6.6 |
| Fusarium | merismoides | IFO 30040 | 125.7 | 16.2 |
| Ganoderma | lucidum | IFO 31863 | 2.1 | 31.8 |
| Glomerella | cingulata | IFO 5257 | 47.8 | 78.7 |
| Laetiporus | sulphureusII | | 66.9 | 32.8 |
| Lentinus | lepideus | TD-832 | 165.2 | 35.1 |
| Lenzites | betulina | IFO 8715 | 155.9 | 34.5 |
| Macrophoma | commelinae | IFO 9569 | 210.2 | 99.3 |
| Monascus | purpureus | IFO 5965 | 135.7 | 13.7 |
| Mortierella | isabellina | IFO 7829 | 8.7 | 100.0 |
| Paecilomyces | varioti | HUT 4028 | 34.6 | 100.0 |
| Penicillium | chermesinum | IFO 5800 | 39.9 | 86.7 |
| Penicillium | chrysogenum | IFO 4640 | 133.8 | 97.4 |
| Penicillium | expansum | IFO 5854 | 4.5 | 51.1 |
| Penicillium | lilacinium | IFO31914 | 47.2 | 95.1 |
| Phialophora | fastigiata | IFO 6850 | 38.4 | 89.4 |

TABLE 4-continued

| Microorganism | | | Output (ug/ml) | D.E. (%) |
|---|---|---|---|---|
| Pholiota | aurivella | IFO 30265 | 74.5 | 100.0 |
| Pholiota | limonella | IFO 31868 | 0.8 | 100.0 |
| Pleurotus | dryinus | | 123.9 | 26.0 |
| Pleurotus | ostreatus | | 159.1 | 22.4 |
| Pleurotus | porrigens | | 247.7 | 87.3 |
| Scopulariopsis | brevicaulis | IFO 4843 | 88.6 | 23.9 |
| Sehizophyllum | commune | IFO 6503 | 119.9 | 43.7 |
| Sporotrichum | aurantiacum | IFO 9381 | 84.4 | 8.9 |
| Zygorhynchus | moelleri | HUT 1305 | 167.6 | 93.5 |

EXAMPLE 14

(3R,5S)-6-benzoyloxy-3,5-dihydroxyhexanoic tert-butyl ester

Using 5 ml of Medium D described hereinbefore, the microorganisms indicated in Table 5 were cultured in the same manner as in Example 13. Then, the same reaction was carried out. The results are shown in Table 5.

TABLE 5

| Microorganism | | | Output (µg/ml) | D.E. (%) |
|---|---|---|---|---|
| Microtetraspora | roseoviolacea | IFO 14098 | 27.8 | 15.4 |
| Streptomyces | achromogenes subsp. rubradiris | IFO 14000 | 1.6 | 19.3 |
| Streptomyces | sp. | | 29.4 | 42 |
| Streptomyces | aureus | NIHJ 122 | 1 | 100 |

EXAMPLE 15

(3R,5S)-6-benzoyloxy-3,5-dihydroxyhexanoic tert-butyl ester

A Sakaguchi flask of 500 ml capacity was charged with 100 ml of a medium composed of Bacto-tryptone 1.6%, Bacto-yeast extract 1%, and sodium chloride 1% (pH 7.0) and, after sterilization, inoculated with *Escherichia coli* HB101 (pNTCRG); FERM BP-6898 (deposited with National Institute of Bioscience and Human-Technology (1-3, Higashi 1-chome, Tsukuba-shi, Ibaraki, Japan) as of Sep. 28, 1999). Shake culture was carried out at 37° C. for 12 hours. After completion of cultivation, 1 g of (5S)-6-benzoyloxy-5-hydroxy-3-oxohexanoic tert-butyl ester, 610 mg of glucose, and 3 mg of oxidized nicotinamide-adenine dinucleotide phosphate were added and the reaction was conducted for 24 hours, during which the pH was maintained at 6.5 with sodium hydroxide. After completion of the reaction, the cells were centrifugally removed and the supernatant was extracted with 2 portions of ethyl acetate, 100 mL each. The organic phase obtained was dehydrated over anhydrous sodium sulfate and the solvent was distilled off under reduced pressure to give 900 mg of 6-benzoyloxy-3,5-dihydroxyhexanoic tert-butyl ester as oil. As analyzed by the method described in Example 11, the diastereomer ratio of this product was (3R,5S)/(3S,5S)=99.5/0.5.

$^1$H-NMR (CDCl$_3$, 400 MHz/ppm); 1.47 (9H, s), 1.63–1.82 (2H, m), 2.45 (2H, d), 4.1–4.3 (4H, m), 7.32–7.7 (3H, m), 8.0–8.22 (2H, m) IR (neat); 3450, 3000, 1730, 1040, 850, 720 cm$^{-1}$

EXAMPLE 16

2-[(4R,6S)-2,2-dimethyl-6-benzoyloxymethyl-1,3-dioxan-4-yl]acetic tert-butyl ester To a solution composed of 8.94 g (27.6 mmol) of (5S)-6-benzoyloxy-3,5-dihydroxyhexanoic tert-butyl ester produced in Example 15, 35.8 mL of 2,2-dimethoxypropane, and 2.5 mL of methylene chloride was added 269 mg (1.4 mmol) of p-toluenesulfonic acid·1H$_2$O, and the mixture was stirred at 20° C. for 4 hours, after which 500 mL of saturated sodium hydrogen carbonate solution was added. The aqueous layer was separated and further extracted with 2 portions of methylene chloride, 20 mL each, and the organic layers were combined. The combined solution was dehydrated over anhydrous sodium sulfate and the solvent was distilled off under reduced pressure to give a colorless oil. This residue was purified by silica gel column chromatography (Kieselgel 60, product of Merck; hexane:acetone=10:1) to give 7.24 g of 2-[(4R,6S)-2,2-dimethyl-6-benzoyloxymethyl-1,3-dioxan-4-yl]acetic tert-butyl ester (white solid). Yield: 72%.

$^1$H-NMR (CDCl$_3$, 400 MHz/ppm); 1.44 (9H, s), 1.45 (6H, d), 1.55–1.59 (2H, m), 2.35–2.46 (2H, m), 4.22–4.37 (4H, m), 7.43–7.59 (3H, m), 8.0–8.1 (2H, m) IR (neat); 2975, 1720, 1270, 1150, 1100, 718 cm$^{-1}$ m.p. 55 to 56° C.

EXAMPLE 17

2-[(4R,6S)-2,2-dimethyl-6-benzoyloxymethyl-1,3-dioxan-4-yl]acetic tert-butyl ester To a solution composed of 108 mg (90.2 weight %, 0.3 mmol) of the (5S)-6-benzoyloxy-3,5-dihydroxyhexanoic tert-butyl ester produced in Example 15, 62.4 mg (0.6 mmol) of 2,2-dimethoxypropane, and 5 mL of acetone was added 5.7 mg (0.03 mmol) of p-toluenesulfonic acid·1H$_2$O, and the mixture was stirred at 40° C. for 16 hours. This reaction mixture was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The compositional yield values were as follows.

2-[(4R,6S)-2,2-dimethyl-6-benzoyloxymethyl-1,3-dioxan-4-yl]acetic tert-butyl ester: 78.8%; (5S)-6-benzoyloxy-3,5-dihydroxyhexanoic tert-butyl ester: 7.5%; (2S,4R)-4-hydroxy-6-oxo-2-[(benzoyloxy)methyl]tetrahydro-2H-pyran: 5.9%; 2-[(4R,6S)-2,2-dimethyl-6-benzoyloxymethyl-1,3-dioxan-4-yl]acetic methyl ester: 3.0%.

EXAMPLE 18

2-[(4R,6S)-2,2-dimethyl-6-benzoyloxymethyl-1,3-dioxan-4-yl]acetic tert-butyl ester To a solution composed of 108 mg (90.2 weight %, 0.3 mmol) of the (5S)-6-benzoyloxy-3,5-dihydroxyhexanoic tert-butyl ester produced in Example 15, 62.4 mg (0.6 mmol) of 2,2-dimethoxypropane, and 5 mL of acetone were added 5.7 mg (0.03 mmol) of p-toluenesulfonic acid·1H$_2$O and 11.9 mg (0.15 mmol) of pyridine, and the mixture was stirred at 40° C. for 16 hours. This reaction mixture was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The compositional yield values were as follows.

2-[(4R,6S)-2,2-dimethyl-6-benzoyloxymethyl-1,3-dioxan-4-yl]acetic tert-butyl ester: 93.1%; (5S)-6-benzoyloxy-3,5-dihydroxyhexanoic tert-butyl ester: 3.4%; (2S,4R)-4-hydroxy-6-oxo-2-[(benzoyloxy)methyl]tetrahydro-2H-pyran: 0.1%; 2-[(4R,6S)-2,2-dimethyl-6-benzoyloxymethyl-1,3-dioxan-4-yl]acetic methyl ester: 0.1%.

EXAMPLE 19

2-[(4R,6S)-2,2-dimethyl-6-benzoyloxymethyl-1,3-dioxan-4-yl]acetic tert-butyl ester To a solution composed of 108 mg (90.2 weight %, 0.3 mmol) of the (5S)-6-benzoyloxy-3,5-dihydroxyhexanoic tert-butyl ester produced in Example 15, 62.4 mg (0.6 mmol) of 2,2-dimethoxypropane, and 5 mL of acetone were added 5.7 mg (0.03 mmol) of p-toluenesulfonic acid·1H$_2$O and 15.2 mg (0.15 mmol) of triethylamine, and the mixture was stirred at 40° C. for 16 hours. This reaction mixture was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The compositional yield values were as follows.

2-[(4R,6S)-2,2-dimethyl-6-benzoyloxymethyl-1,3-dioxan-4-yl]acetic tert-butyl ester: 93.3%; (5S)-6-benzoyloxy-3,5-dihydroxyhexanoic tert-butyl ester: 3.0%; (2S, 4R)-4-hydroxy-6-oxo-2-[(benzoyloxy)methyl]tetrahydro-2H-pyran: 0.1%; 2-[(4R, 6S)-2,2-dimethyl-6-benzoyloxymethyl-1,3-dioxan-4-yl]acetic methyl ester: 0.1%.

EXAMPLE 20

2-[(4R,6S)-2,2-dimethyl-6-benzoyloxymethyl-1,3-dioxan-4-yl]acetic tert-butyl ester To a solution composed of 108 mg (90.2 weight %, 0.3 mmol) of the (5S)-6-benzoyloxy-3,5-dihydroxyhexanoic tert-butyl ester produced in Example 15, 62.4 mg (0.6 mmol) of 2,2-dimethoxypropane, and 5 mL of acetone were added 5.7 mg (0.03 mmol) of p-toluenesulfonic acid.1H$_2$O and 10.2 mg (0.15 mmol) of imidazole, and the mixture was stirred at 40° C. for 16 hours. This reaction mixture was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The compositional yield values were as follows.

2-[(4R,6S)-2,2-dimethyl-6-benzoyloxymethyl-1,3-dioxan-4-yl]acetic tert-butyl ester: 93.9%; (5S)-6-benzoyloxy-3,5-dihydroxyhexanoic tert-butyl ester: 3.0%; (2S,4R)-4-hydroxy-6-oxo-2-[(benzoyloxy)methyl]tetrahydro-2H-pyran: 0.1%; 2-[(4R,6S)-2,2-dimethyl-6-benzoyloxymethyl-1,3-dioxan-4-yl]acetic methyl ester: 0.1%.

EXAMPLE 21

2-[(4R,6S)-2,2-dimethyl-6-benzoyloxymethyl-1,3-dioxan-4-yl]acetic tert-butyl ester To a solution composed of 108 mg (90.2 weight %, 0.3 mmol) of the (5S)-6-benzoyloxy-3,5-dihydroxyhexanoic tert-butyl ester produced in Example 15, 62.4 mg (0.6 mmol) of 2,2-dimethoxypropane, and 5 mL of acetone were added 5.7 mg (0.03 mmol) of p-toluenesulfonic acid.1H$_2$O and 14.0 mg (0.15 mmol) of 3-methylpyridine, and the mixture was stirred at 40° C. for 16 hours. This reaction mixture was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The compositional yield values were as follows.

2-[(4R,6S)-2,2-dimethyl-6-benzoyloxymethyl-1,3-dioxan-4-yl]acetic tert-butyl ester: 93.8%; (5S)-6-benzoyloxy-3,5-dihydroxyhexanoic tert-butyl ester: 2.8%; (2S,4R)-4-hydroxy-6-oxo-2-[(benzoyloxy)methyl]tetrahydro-2H-pyran: 0.1%; 2-[(4R,6S)-2,2-dimethyl-6-benzoyloxymethyl-1,3-dioxan-4-yl]acetic methyl ester: 0.1%.

EXAMPLE 22

2-[(4R,6S)-2,2-dimethyl-6-benzoyloxymethyl-1,3-dioxan-4-yl]acetic tert-butyl ester To a solution composed of 108 mg (90.2 weight %, 0.3 mmol) of the (5S)-6-benzoyloxy-3,5-dihydroxyhexanoic tert-butyl ester produced in Example 15, 62.4 mg (0.6 mmol) of 2,2-dimethoxypropane, and 5 mL of acetone were added 5.7 mg (0.03 mmol) of p-toluenesulfonic acid.1H$_2$O and 18.3 mg (0.15 mmol) of N,N-dimethylaminopyridine, and the mixture was stirred at 40° C. for 16 hours. This reaction mixture was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The compositional yield values were as follows.

2-[(4R,6S)-2,2-dimethyl-6-benzoyloxymethyl-1,3-dioxan-4-yl]acetic tert-butyl ester: 93.8%; (5S)-6-benzoyloxy-3,5-dihydroxyhexanoic tert-butyl ester: 2.3%; (2S,4R)-4-hydroxy-6-oxo-2-[(benzoyloxy)methyl]tetrahydro-2H-pyran: 0.1%; 2-[(4R,6S)-2,2-dimethyl-6-benzoyloxymethyl-1,3-dioxan-4-yl]acetic methyl ester: 0.1%.

EXAMPLE 23

2-[(4R,6S)-2,2-dimethyl-6-benzoyloxymethyl-1,3-dioxan-4-yl]acetic tert-butyl ester To a solution composed of 108 mg (90.2 weight %, 0.3 mmol) of the (5S)-6-benzoyloxy-3,5-dihydroxyhexanoic tert-butyl ester produced in Example 15, 62.4 mg (0.6 mmol) of 2,2-dimethoxypropane, and 5 mL of acetone were added 3.0 mg (0.03 mmol) of methanesulfonic acid and 11.9 mg (0.15 mmol) of pyridine, and the mixture was stirred at 40° C. for 16 hours. This reaction mixture was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The compositional yield values were as follows.

2-[(4R,6S)-2,2-dimethyl-6-benzoyloxymethyl-1,3-dioxan-4-yl]acetic tert-butyl ester: 95.6%; (5S)-6-benzoyloxy-3,5-dihydroxyhexanoic tert-butyl ester: 2.6%; (2S,4R)-4-hydroxy-6-oxo-2-[(benzoyloxy)methyl]tetrahydro-2H-pyran: 0.1%; 2-[(4R,6S)-2,2-dimethyl-6-benzoyloxymethyl-1,3-dioxan-4-yl]acetic methyl ester: undetected.

EXAMPLE 24

2-[(4R,6S)-2,2-dimethyl-6-benzoyloxymethyl-1,3-dioxan-4-yl]acetic tert-butyl ester To a solution composed of 108 mg (90.2 weight %, 0.3 mmol) of the (5S)-6-benzoyloxy-3,5-dihydroxyhexanoic tert-butyl ester produced in Example 15, 62.4 mg (0.6 mmol) of 2,2-dimethoxypropane, and 5 mL of acetone were added 3.5 mg (0.03 mmol) of trifluoroacetic acid and 11.9 mg (0.15 mmol) of pyridine, and the mixture was stirred at 40° C. for 16 hours. This reaction mixture was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The compositional yield values were as follows.

2-[(4R,6S)-2,2-dimethyl-6-benzoyloxymethyl-1,3-dioxan-4-yl]acetic tert-butyl ester: 89.3%; (5S)-6-benzoyloxy-3,5-dihydroxyhexanoic tert-butyl ester: 8.8%; (2S,4R)-4-hydroxy-6-oxo-2-[(benzoyloxy)methyl]tetrahydro-2H-pyran: 0.1%; 2-[(4R,6S)-2,2-dimethyl-6-benzoyloxymethyl-1,3-dioxan-4-yl]acetic methyl ester: undetected.

EXAMPLE 25

2-[(4R,6S)-2,2-dimethyl-6-benzoyloxymethyl-1,3-dioxan-4-yl]acetic tert-butyl ester To a solution composed of 108 mg (90.2 weight %, 0.3 mmol) of the (5S)-6-benzoyloxy-3,5-dihydroxyhexanoic tert-butyl ester produced in Example 15, 62.4 mg (0.6 mmol) of 2,2-dimethoxypropane, and 5 mL of acetone were added 1.5 mg (0.015 mmol) of sulfuric acid and 11.9 mg (0.15 mmol) of pyridine, and the mixture was stirred at 40° C. for 16 hours. This reaction mixture was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The compositional yield values were as follows.

2-[(4R,6S)-2,2-dimethyl-6-benzoyloxymethyl-1,3-dioxan-4-yl]acetic tert-butyl ester: 95.8%; (5S)-6-benzoyloxy-3,5-dihydroxyhexanoic tert-butyl ester: 2.3%; (2S,4R)-4-hydroxy-6-oxo-2-[(benzoyloxy)methyl]tetrahydro-2H-pyran: 0.1%; 2-[(4R,6S)-2,2-dimethyl-6-benzoyloxymethyl-1,3-dioxan-4-yl]acetic methyl ester: undetected.

EXAMPLE 26

Purification of 2-[(4R,6S)-2,2-dimethyl-6-benzoyloxymethyl-1,3-dioxan-4-yl]acetic tert-butyl ester To a solution composed of 3.24 g (90.2 weight %, 9.0 mmol) of the (5S)-6-benzoyloxy-3,5-dihydroxyhexanoic tert-butyl ester produced in Example 15, 2.12 g (18.0 mmol) of 2,2-dimethoxypropane, and 5 mL of acetone was added 95 mg (0.45 mmol) of p-toluenesulfonic acid. $1H_2O$, and the mixture was stirred at 40° C. for 4 hours. The solvent was distilled off under reduced pressure and the residue was extracted using 25 mL of ethyl acetate and 10 mL of saturated aqueous sodium hydrogen carbonate. After separation of the aqueous layer, the organic layer was further washed with 10 mL of water. The solvent was then distilled off under reduced pressure to give 3.764 g of a colorless oil. This oil was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The compositional yield values were as follows.

2-[(4R,6S)-2,2-dimethyl-6-benzoyloxymethyl-1,3-dioxan-4-yl]acetic tert-butyl ester: 79.7 weight %. As impurities, (5S)-6-benzoyloxy-3,5-dihydroxyhexanoic tert-butyl ester: 0.1 weight %; (2S,4R)-4-hydroxy-6-oxo-2-[(benzoyloxy)methyl]tetrahydro-2H-pyran: 0.1 weight %; 2-[(4R,6S)-2,2-dimethyl-6-benzoyloxymethyl-1,3-dioxan-4-yl]acetic methyl ester: 5.0 weight %; 2-[(4S,6S)-2,2-dimethyl-6-benzoyloxymethyl-1,3-dioxan-4-yl]acetic tert-butyl ester: 0.2 weight % were contained.

To the above oil was added 30 mL of hexane, and the mixture was cooled to −30° C. (treatment concentration: 10% (substrate weight/solution volume)). About 10 mg of seed crystals were added and the mixture was further stirred vigorously at the same temperature for 1 hour. The crystals separating out were collected by suction filtration, drained thoroughly, and washed with 10 mL of cold hexane. The crystal crop was then dried in vacuo (ca 1 to 5 mmHg, 20 to 40° C., 2 hours) to obtain 2.46 g of 2-[(4R,6S)-2,2-dimethyl-6-benzoyloxymethyl-1,3-dioxan-4-yl]acetic tert-butyl ester as crystals (crystallization recovery rate 81%). Analysis of the above crystals showed a purity of 97.2 weight % (96.8 area %). As impurities, the crystal crop contained: 2-[(4R,6S)-2,2-dimethyl-6-benzoyloxymethyl-1,3-dioxan-4-yl]acetic methyl ester: 2.8 weight % (2.8 area %); (5S)-6-benzoyloxy-3,5-dihydroxyhexanoic tert-butyl ester: undetected; (2S,4R)-4-hydroxy-6-oxo-2-[(benzoyloxy)methyl]tetrahydro-2H-pyran: undetected; 2-[(4S,6S)-2,2-dimethyl-6-benzoyloxymethyl-1,3-dioxan-4-yl]acetic tert-butyl ester: undetected.

EXAMPLE 27

Purification of 2-[(4R,6S)-2,2-dimethyl-6-benzoyloxymethyl-1,3-dioxan-4-yl]acetic tert-butyl ester To a solution composed of 3.24 g (90.2 weight %, 9.0 mmol) of the (5S)-6-benzoyloxy-3,5-dihydroxyhexanoic tert-butyl ester produced in Example 15, 2.12 g (18.0 mmol) of 2,2-dimethoxypropane, and 5 mL of acetone was added 95 mg (0.45 mmol) of p-toluenesulfonic acid.$1H_2O$, and the mixture was stirred at 40° C. for 4 hours. The solvent was then distilled off under reduced pressure and the residue was extracted using 25 mL of ethyl acetate and 10 mL of saturated aqueous sodium hydrogen carbonate. After separation of the aqueous layer, the organic layer was further washed with 10 mL of water. The solvent was then distilled off under reduced pressure to give 3.764 g of a colorless oil. This oil was analyzed by high-performance liquid chromatography (column: Develosil ODS-HG-3 4.6×250 mm, product of Nomura Chemical, eluent: water/acetonitrile=50/50, flow rate: 1.0 mL/min, detector: UV 220 nm, column temperature: 40° C.). The compositional yield values were as follows.

2-[(4R,6S)-2,2-dimethyl-6-benzoyloxymethyl-1,3-dioxan-4-yl]acetic tert-butyl ester: 86.0 weight %. As impurities, (5S)-6-benzoyloxy-3,5-dihydroxyhexanoic tert-butyl ester: 0.1 weight %; (2S,4R)-4-hydroxy-6-oxo-2-[(benzoyloxy)methyl]tetrahydro-2H-pyran: 0.1 weight %; 2-[(4R,6S)-2,2-dimethyl-6-benzoyloxymethyl-1,3-dioxan-4-yl]acetic methyl ester: 5.4 weight %; 2-[(4S,6S)-2,2-dimethyl-6-benzoyloxymethyl-1,3-dioxan-4-yl]acetic tert-butyl ester: 0.2 weight % were contained.

To the above oil was added 30 mL of methylcyclohexane, and the mixture was cooled to −30° C. (treatment concentration: 10% (substrate weight/solution volume)). About 10 mg of seed crystals were added and the mixture was further stirred vigorously at the same temperature for 1 hour. The crystals separating out were collected by suction filtration, drained thoroughly, and washed with 10 mL of cold methylcyclohexane. The crystal crop was then dried in vacuo (ca 1 to 5 mmHg, 20 to 40° C., 2 hours) to obtain 2.24 g of 2-[(4R,6S)-2,2-dimethyl-6-benzoyloxymethyl-1,3-dioxan-4-yl]acetic tert-butyl ester as crystals (crystallization recovery rate 74%). Analysis of the above crystals showed a purity of 97.2 weight % (96.8 area %). As impurities, the crystal crop contained: 2-[(4R,6S)-2,2-dimethyl-6-benzoyloxymethyl-1,3-dioxan-4-yl]acetic methyl ester: 2.8 weight % (2.8 area %); (5S)-6-benzoyloxy-3,5-dihydroxyhexanoic tert-butyl ester: undetected; (2S,4R)-4-hydroxy-6-oxo-2-[(benzoyloxy)methyl]tetrahydro-2H-pyran: undetected; 2-[(4S,6S)-2,2-dimethyl-6-benzoyloxymethyl-1,3-dioxan-4-yl]acetic tert-butyl ester: undetected.

EXAMPLE 28

2-[4R,6S]-6-(hydroxymethyl)-2,2-dimethyl-1,3-dioxan-4-yl]acetic tert-butyl ester To a solution of 3.64 g (10 mmol) of the 2-[(4R,6S)-2,2-dimethyl-6-benzoyloxymethyl-1,3-dioxan-4-yl]acetic tert-butyl ester produced in Example 26 in methanol (36 mL) was added 10 mL of 1N-aqueous sodium hydroxide solution, and the mixture was stirred at room temperature for 2 hours. This reaction mixture was adjusted to pH 7 by gradual addition of 1N-hydrochoric acid under ice-cooling. The methanol was then distilled off under reduced pressure and the residual aqueous solution was extracted with 2 portions of methylene chloride, 70 mL each. The organic layer was dehydrated over anhydrous sodium sulfate and the solvent was distilled off under reduced pressure to give a colorless oil. This residue was purified by silica gel column chromatography (Kieselgel 60, product of Merck; hexane:acetone=5:1) to give 2.34 g of 2-[(4R,6S)-6-(hydroxymethyl)-2,2-dimethyl-1,3-dioxan-4-yl]acetic tert-butyl ester (white solid). Yield 90%.

$^1$H-NMR (CDCl$_3$, 400 MHz/ppm); 1.29–1.52 (2H, m), 1.39 (3H, m), 1.45 (9H, s), 1.47 (3H, s), 2.05 (1H, bs), 2.33 (1H, dd), 2.44 (1H, dd), 3.47–3.53 (1H, m), 3.99–4.04 (1H, m), 4.27–4.33 (1H, m) IR (neat); 2980, 1720, 1365, 1200, 1150, 1020 cm$^{-1}$.

INDUSTRIAL APPLICABILITY

In accordance with the present invention constituted as above, pharmaceutical intermediates, particularly optically active 2-[6-(hydroxymethyl)-1,3-dioxan-4-yl]acetic acid derivatives which are of value as intermediates of HMG-CoA reductase inhibitors, can be produced from inexpensive, readily available starting materials without using any extraordinary equipment such as a low-temperature reactor.

The invention claimed is:

1. A production process of a following compound (I);

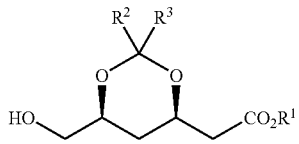
(I)

in the formula, R$^1$ represents a hydrogen, an alkyl group of 1 to 12 carbon atoms, an aryl group of 6 to 12 carbon atoms, or an aralkyl group of 7 to 12 carbon atoms; R$^2$ and R$^3$ each independently represents a hydrogen, an alkyl group of 1 to 12 carbon atoms, an aryl group of 6 to 12 carbon atoms, or an aralkyl group of 7 to 12 carbon atoms, and R$^2$ and R$^3$ may jointly form a ring, which comprises (1) reacting an enolate prepared by permitting a base or a 0-valent metal to act on an acetic acid ester derivative represented by the following formula (II);

X$^1$CH$_2$CO$_2$R$^1$  (II)

in the formula, R$^1$ is as defined above; and X$^1$ represents a hydrogen or a halogen atom, with (S)-β-hydroxy-γ-butyrolactone represented by the following formula (III);

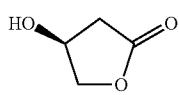
(III)

at a temperature not lower than −30° C. to produce a compound represented by the following formula (IV);

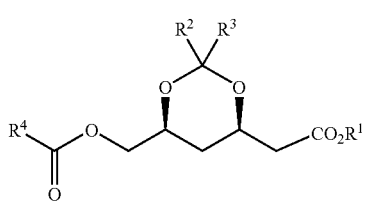
(VII)

in the formula, R$^1$, R$^2$, R$^3$, and R$^4$ are as defined above, and (5) subjecting this compound to solvolysis in the presence of a base to form the compound formula (I).

2. The production process according to claim 1 wherein X$^1$ of the acetic acid ester derivative (II) is a hydrogen atom and a magnesium amide represented by the following formula (VIII);

(VIII)

in the formula, R$^5$ and R$^6$ each independently represents an alkyl group of 1 to 12 carbon atoms, an aryl group of 6 to 12 carbon atoms, an aralkyl group of 7 to 12 carbon atoms, or a silyl group;

and X$^2$ represents a halogen atom, is used as the base in preparing the enolate.

3. The production process according to claim 2 wherein, of the magnesium amide (VIII), each of R$^5$ and R$^6$ is an isopropyl group and X$^2$ is a chlorine atom.

4. The production process according to claim 1 wherein X$^1$ of the acetic acid ester derivative (II) is a halogen atom and magnesium or zinc is used as the 0-valent metal in preparing the enolate.

5. The production process according to claim 1 wherein the reaction of the enolate with (S)β-hydroxy-γ-butyrolactone (III) is carried out in the presence of polyether.

6. The production process according to claim 5 wherein dimethoxyethane is used as the polyether.

7. The production process according to claim 1 wherein (S)-β-hydroxy-γ-butyrolactone represented by the following formula (III);

(III)

is treated, in advance, with a Grignard reagent represented by the following formula (IX);

R$^7$—Mg—X$^3$  (IX)

in the formula, R$^7$ represents an alkyl group of 1 to 12 carbon atoms, an aryl group of 6 to 12 carbon atoms, or an aralkyl group of 7 to 12 carbon atoms; and X$^3$ represents a halogen atom, and then the obtained product as reacted, at a temperature not lower than −30° C., with the enolate prepared by permitting the base or the 0-valent metal to act on the acetic acid ester derivative represented by the following formula (II);

X$^1$CH$_2$CO$_2$R$^1$  (II)

in the formula, R$^1$ and X$^1$ are as defined above, to produce the compound represented by the following formula (IV);

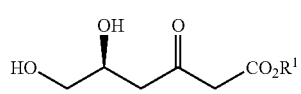
(IV)

in the formula, $R^1$ is as defined above.

8. The production process according to claim 7 wherein, of the Grignard reagent (IX), $R^7$ is a tert-butyl group and $X^3$ is a chlorine atom.

9. The production process according claim 1 wherein (S)-β-hydroxy-γ-butyrolactone (III) is treated with a base and a magnesium compound in advance and reacted, at a temperature not low than −30° C., with the enolate prepared by permitting the base or the 0-valent metal to act on the acetic acid ester derivative (II) to produce the compound represented by the above formula (V).

10. The production process according to claim 9 wherein the base is sodium hydride, lithium diisopropylamide, or chloromagnesium diisopropylamide.

11. The production process according to claim 9 wherein the magnesium compound is magnesium chloride or magnesium bromide.

12. The production process according to claim 7 wherein $X^1$ of the acetic acid ester derivative (II) is a hydrogen atom and
a lithium amide represented by the following formula (X);

(X)

in the formula, $R^8$ and $R^9$ each independently represents an alkyl group of 1 to 12 carbon atoms, an aryl group of 6 to 12 carbon atoms, an aralkyl group of 7 to 12 carbon atoms, or a silyl group,
is used as the base in preparing the enolate.

13. The production process according to claim 12 wherein, of the lithium amide (X), each of $R^8$ and $R^9$ is an isopropyl group.

14. The production process according to claim 7 wherein $X^1$ of the acetic acid ester derivative (II) is a halogen atom and
magnesium or zinc is used as the 0-valent metal in preparing the enolate.

15. The production process according to claim 1 wherein, in the acylation step, a compound represented by the following formula (XI);

(XI)

or a compound represented by the following formula (XVI);

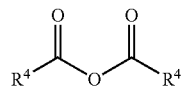
(XVI)

in the above formulas, $R^4$ represents a hydrogen, an alkyl group of 1 to 12 carbon atoms, an aryl group of 6 to 12 carbon atoms, or an aralkyl group of 7 to 12 carbon atoms; and Q represents a leaving group,
is used as the acylating agent.

16. The production process according to claim 15 wherein Q of the acylating agent (XI) is a halogen atom.

17. The production process according to claim 16 wherein the halogen atom is a chlorine atom.

18. The production process according to claim 1 wherein an amine is used as the base in the acylation step.

19. The production process according to claim 18 wherein triethylamine or pyridine is used as the amine.

20. The production process according to claim 1 wherein, in the acylation step (2), the compound represented by the following formula (V);

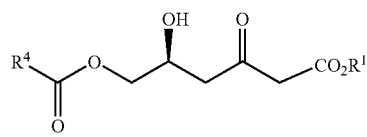
(V)

in the formula, $R^1$ and $R^4$ are as defined above,
is treated with an aliphatic hydrocarbon solvent to remove the impurity contaminating the compound represented by the above formula (V) and
the compound represented by the above formula (V) is obtained in a crystal form.

21. The production process according to claim 20 wherein the impurity contaminating the compound represented by the above formula (V) is a compound represented by the following formula (XII);

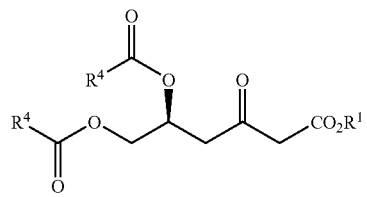
(XII)

in the formula, $R^1$ and $R^4$ are as defined above.

22. The production process according to claim 20 wherein the aliphatic hydrocarbon solvent is pentane, hexane, methylcyclohexane, heptane, octane, or isooctane.

23. The production process according to claim 20 wherein the crystallization is carried out with additional use of an auxiliary solvent,
said solvent being used for a purpose of improving at least one of a solubility, yield, treatment concentration, effect of purification, and physical properties of obtainable crystals of the compound represented by the above formula (V).

24. The production process according to claim 23 wherein the auxiliary solvent is used in such an amount that the weight ratio of said auxiliary solvent and the aliphatic hydrocarbon solvent (said auxiliary solvent/ aliphatic hydrocarbon solvent) is not greater than 1 at completion of the procedure for crystallization.

25. The production process according to claim 23 wherein the auxiliary solvent is at least one species selected from the group consisting of toluene, ethyl acetate, methyl tert-butyl ether and methylene chloride.

26. The production process according to claim 1 wherein a culture broth, cells or processed cells of the microorganism is used in the reduction step using the microorganism, said microorganism for use being selected from among microorganisms belonging to the genera *Ashbya, Botryoascus, Brettanomyces, Candida, Citeromyces, Clavispora, Cryptococcus, Debaryomyces, Dekkera, Dipodascus, Galactomyces, Geotrichum, Hanseniaspora, Hansenula, Hormoascus, Hyphopichia, Issatchenkia, Kluyveromyces, Komagataella, Lipomyces, Metschnikowia, Nakazawaea, Ogataea, Pachysolen, Pichia, Rhodotorula, Rhodsporidium, Saccharomyces, Saccharomycodes, Saccharomycopsis, Saturnospora, Schizoblastosporion, Schizosaccharomyces, Schwanniomyces, Sporidiobolus, Sporobolomyces, Torulaspora, Torulopsis, Trichosporon, Trigonopsis, Willopsis, Yamadazyma, Zygosaccharomyces, Acidiphilium, Aerobacter, Alcaligenes, Arthrobacter, Aureobacterium, Bacillus, Brevibacterium, Buttiauxella, Cedecea, Cellulomonas, Citrobacter, Clostridium, Comamonas, Corynebacterium, Enterobacter, Erwinia, Escherichia, Flavobacterium, Klebsiella, Luteococcus, Microbacterium, Micrococcus, Ochrobactrum, Proteus, Providencia, Pseudomonas, Rhodococcus, Sarcina, Serratia, Sphingobacterium, Tsukamurella, Absidia, Acremonium, Aegerita, Agrocybe, Amylostereum, Aspergillus, Byssochlamys, Chaetomidium, Chaetosartorya, Cladosporium, Coprinus, Crinipellis, Endophragmia, Flavolus, Fomitopsis, Fusarium, Ganoderma, Glomerella, Laetiporus, Lentinus, Lenzites, Macrophoma, Monascus, Mortierella, Paecilomyces, Penicillium, Phialophora, Pholiota, Pleurotus, Scopulariopsis, Sehizophyllum, Sporotrichum, Zygorhynchus, Microtetraspora,* and *Streptomyces.*

27. The production process according to claim 1 wherein the microorganism for use in the reduction step using the microorganism is selected from the group consisting of *Ashbya gossypii, Botryoascus synnaedendrus, Brettanomyces custersianus, Candida arborea, Candida catenulata, Candida fennica, Candida galacta, Candida haemulonti, Candida magnoliae, Candida musae, Candida nitratophila, Candida parapsilosis, Candida pararugosa, Candida stellata, Citeromyces matritensis, Clavispora lusitaniae, Cryptococcus laurentii, Debaryomyces carsonii, Debaryomyces hansenii* var. *fabryi, Debaryomyces hansenii* var. *hansenii, Debaryomyces kloeckeri, Debaryomyces marama, Debaryomyces pseudopolymorphus, Debaryomyces robertsiae, Debaryomyces* sp., *Dekkera anomala, Dipodascus armillariae, Dipodascus ovetensis, Dipodascus tetrasperma, Galactomyces reessii, Geotrichum candidum, Geotrichum fermentans, Geotrichum fragrans, Geotrichum loubieri, Hanseniaspora guilliermondii, Hansenula methanolosa, Hansenula polymorpha, Hormoascus philentomus, Hormoascus platypodis, Hyphopichia burtonii, Issatchenkia orientalis, Issatchenkia terricola, Kluyveromyces lactis, Kluyveromyces marxianus, Kluyveromyces polysporus, Kluyveromyces thermotolerans, Komagataella pastoris, Lipomyces starkeyi, Metschnikowia bicuspidata, Metschnikowia pulcherrima, Nakazawaea holstii, Ogataea minuta* var. *minuta, Ogataea pini, Ogataea polymorpha, Ogataea wickerhamii, Pachysolen tannophilus, Pichia canadensis, Pichia farinose, Pichia jandinii, Pichia saitoi, Pichia toletana, Pichia triangularis, Pichia wickerhamii, Rhodotorula graminis, Rhodotorula minuta, Rhodsporidium diobovatum, Rhodsporidium toruloides, Saccharomyces bayanus, Saccharomyces pastorianus, Saccharomyces rosei, Saccharomyces sake, Saccharomyces steineri, Saccaromyces unisporus, Saccharomycodes ludwigii, Saccharomycopsis capsularis, Saccharomycopsis malanga, Saturnospora dispora, Schizoblastosporion kobayasii, Schizosaccharomyces pombe, Schwanniomyces occidentalis* var. *occidentalis, Sporidiobolus johnsonii, Sporobolomyces pararoseus, Sporobolomyces salmonicolor, Torulaspora delbrueckii, Torulopsis methanolevescens, Torulopsis osboenis, Torulopsis* sp., *Torulopsis uvae, Trichosporon pullulans, Trichosporon* sp. *Trigonopsis variabilis, Willopsis saturnus* var. *mrakii, Willopsis saturnus* var. *saturnus, Yamadazyma farinosa, Yamadazyma haplophila, Zygosaccharomyces naniwensis, Zygosaccharomyces* sp., *Acidiphilium cryptum, Aerobacter cloacae, Alcaligenes xylosoxidans, Alcaligenes xylosoxidans* subsp. *denitrificans, Arthrobacter globiformis, Arthrobacter protophormiae, Aureobacterium esteraromaticum, Bacillus badius, Bacillus sphaericus, Brevibacterium ammomiagenes, Buttiauxella agrestis, Cedecea davisiae, Cellulomonas* sp., *Cellulomonas turbata, Citrobacter freundii, Clostridium cylindrosporum, Comamonas testosteroni, Corynebacterium acectoacidophilum, Corynebacterium ammoniagenes, Corynebacterium glutamicum, Corynebacterium glutamicus, Enterobacter aerogenes, Enterobacter cloacae, Erwinia carotovora* subsp. *carotovora, Escherichia coli, Flavobacterium flavesceus, Klebsiella planticola, Luteococcus japonicus, Microbacterium arborescens, Micrococcus flavus, Micrococcus luteus, Ochrobactrum* sp., *Proteus inconstans, Proteus mirabilis, Proteus rettgeri, Proteus vulgaris, Providencia stuartii, Pseudomonas aeruginosa, Pseudomonas putida, Pseudomonas stutzeri, Rhodococcus equi, Sarcina lutea, Serratia plymuthicum, Serratia proteamaculans* subsp. *proteamaculans, Sphingobacterium spiritivorum, Tsukamurella paurometabolum, Absidia orchidis, Acremonium bacillisporum, Aegerita candida, Agrocybe cylindracea, Amylostereum areolatum, Aspergillus parasiticus, Aspergillus phoenicis, Byssochlamys fulva, Chaetomidium fimeti, Chaetosartorya stromatoides, Cladosporium resinae F. avellaneum, Coprinus cinereus, Coprinus lagopus, Coprinus* sp., *Crinipellis stipitaria, Endophragmia alternata, Flavolus arcularius, Fomitopsis pubertatis, Fusarium merismoides, Ganoderma lucidum, Glomerella cingulata, Laetiporus sulphureus, Lentinus lepideus, Lenzites betulina, Macrophoma commelinae, Monascus purpureus, Mortierella isabellina, Paecilomyces varioti, Penicillium chermesinum, Penicillium chrysogenum, Penicillium expansum, Penicillium lilacinium, Phialophora fastigiata, Pholiota aurivella, Pholiota limonella, Pleurotus dryinus, Pleurotus ostreatus, Pleurotus porrigens, Scopulariopsis brevicaulis, Sehizophyllum commune, Sporotrichum aurantiacum, Zygorhynchus moelleri, Microtetraspora roseoviolacea, Streptomyces achromogenes* subsp. *rubradiris, Streptomyces* sp. and *Streptomyces aureus.*

28. The production process according to claim 1 wherein an amine salt composed of an acid and an amine is used as the acid catalyst in the acetal-forming step.

29. The production process according to claim 28 wherein the amine salt is prepared and used in situ.

30. The production process according to claim 28 wherein the acid is hydrogen chloride, hydrogen bromide, sulfuric acid, methanesulfonic acid, benzenesulfonic acid, p-toluenesulfonic acid or trifluoroacetic acid.

31. The production process according to claim 28 wherein the amine is a tertiary amine.

32. The production process according to claim 31 wherein the tertiary amine is triethylamine, N-methylmorpholine, diisopropylethylamine, pyridine, 2-methylpyridine, 3-methylpyridine, or imidazole.

33. The production process according to claim 28 wherein the amine is used in an excess amount relative to the acid.

34. The production process according to claim 1 wherein the acetal-forming reagent is 2,2-dimethoxypropane.

35. The production process according to claim 1 wherein a compound represented by the following formula (VII);

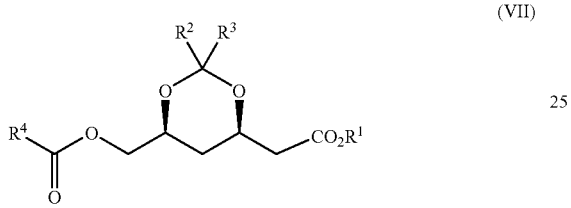

in the formula, $R_1$, $R^2$, $R^3$ and $R^4$ are as defined above, is treated with an aliphatic hydrocarbon solvent to remove the impurity contaminating the compound represented by the above formula (VII) and the compound represented by the above formula (VII) is obtained in a crystal form.

36. The production process according to claim 35 wherein the impurity contaminating the compound represented by the above formula (VII) is at least one compound selected from the group consisting of a compound represented by the following formula (XIII);

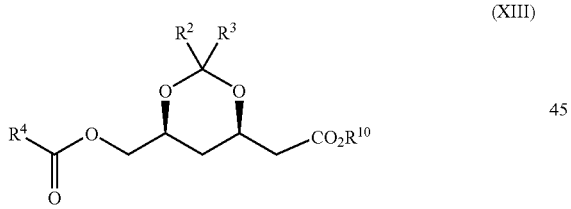

in the formula, $R^2$, $R^3$ and $R^4$ are as defined above; and $R^{10}$ represents a lower alkyl group and is different from $R^1$, a diastereomer represented by the following formula (XIV);

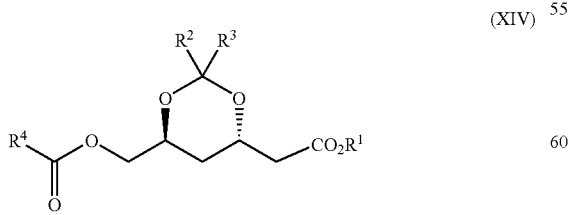

in the formula, $R^1$, $R^2$, $R^3$, and $R^4$ are as defined above, a compound represented by the following formula (XV);

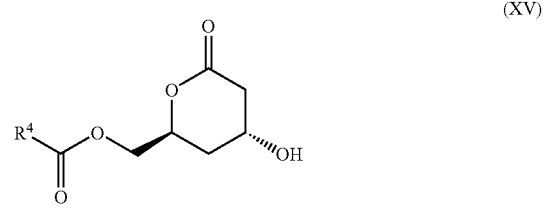

in the formula, $R^4$ is as defined above, and a compound represented by the following formula (VI);

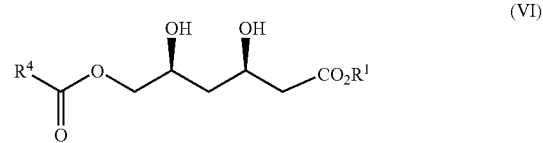

in the formula, $R^1$ and $R^4$ are as defined above.

37. The production process according to claim 36 wherein $R^{10}$ of the compound (XIII) is a methyl group.

38. The production process according to claim 35 wherein the aliphatic hydrocarbon solvent is pentane, hexane, methylcyclohexane, heptane, octane, or isooctane.

39. The production process according to claim 35 wherein the crystallization is carried out with additional use of an auxiliary solvent, said solvent being used for a purpose of improving at least one of a solubility, yield, treatment concentration, effect of purification, and physical properties of obtainable crystals of the compound represented by the above formula (VII).

40. The production process according to claim 39 wherein the auxiliary solvent is used in such an amount that the weight ratio of said auxiliary solvent and the aliphatic hydrocarbon solvent (said auxiliary solvent/aliphatic hydrocarbon solvent) is not greater than 1 at completion of the procedure for crystallization.

41. The production process according to claim 39 wherein the auxiliary solvent is at least one species selected from the group consisting of toluene, ethyl acetate, methyl tert-butyl ether and methylene chloride.

42. The production process according to claim 1 wherein $R^1$ is a tert-butyl group.

43. The production process according to claim 1 wherein each of $R^2$ and $R^3$ is a methyl group.

44. The production process according to claim 1 wherein $R^4$ is a phenyl group.

* * * * *